(12) United States Patent
Rondon et al.

(10) Patent No.: US 8,546,307 B2
(45) Date of Patent: Oct. 1, 2013

(54) TRIPLE TAG SEQUENCE AND METHODS OF USE THEREOF

(75) Inventors: Isaac Rondon, San Francisco, CA (US); Marina Roell, Concord, CA (US); Daniel Bedinger, Vacaville, CA (US)

(73) Assignee: XOMA Technology, Ltd., Berkeley, CA (US)

( * ) Notice: Subject to any disclaimer, the term of this patent is extended or adjusted under 35 U.S.C. 154(b) by 911 days.

(21) Appl. No.: 12/572,877

(22) Filed: Oct. 2, 2009

(65) Prior Publication Data

US 2010/0184612 A1    Jul. 22, 2010

Related U.S. Application Data

(60) Provisional application No. 61/102,672, filed on Oct. 3, 2008, provisional application No. 61/102,675, filed on Oct. 3, 2008.

(51) Int. Cl.
*C40B 30/04* (2006.01)

(52) U.S. Cl.
USPC .................................................. 506/9

(58) Field of Classification Search
None
See application file for complete search history.

(56) References Cited

U.S. PATENT DOCUMENTS

| 5,969,108 | A | 10/1999 | McCafferty et al. |
| 6,057,098 | A | 5/2000 | Buechler et al. |
| 7,094,579 | B2 | 8/2006 | Gray et al. |
| 7,112,439 | B2 | 9/2006 | Johnson et al. |
| 7,396,661 | B2 | 7/2008 | Gray et al. |
| 2003/0199071 | A1 | 10/2003 | Langermann et al. |
| 2004/0202995 | A1 | 10/2004 | de Wildt et al. |
| 2005/0095615 | A1 | 5/2005 | Welch et al. |
| 2008/0108514 | A1 | 5/2008 | Hoogenboom et al. |

FOREIGN PATENT DOCUMENTS

| WO | 03/029456 | 4/2003 |
| WO | WO 2009/126920 A2 * | 10/2009 |

OTHER PUBLICATIONS

Andris-Widhopf et al. (Aug. 2000) Journal of Immunological Methods vol. 242 pp. 159 to 181.*
Evans et al. (Jul. 11, 2006) Proceedings of the National Academy of Sciences USA vol. 103 pp. 10666 to 10671.*
Invitrogen (Dec. 28, 2010) pSecTag2 A B and C Catalog No. V900-20 manual.*
Asada et al., BMC Research Notes (2008) 1:42 "Biologically active fibroblast growth factor 1 tagged with various epitopes".
Hotchkiss et al., TEM8 expression stimulates endothelial cell adhesion and migration by regulating cell-matrix interactions on collagen, Experimental Cell Research 2005, 305(1):133-144.

(Continued)

*Primary Examiner* — Ardin Marschel
*Assistant Examiner* — Christian Boesen
(74) *Attorney, Agent, or Firm* — Diane Wilcock; Jones Day

(57) ABSTRACT

The present disclosure relates to novel triple tag sequences that may comprise a 6× histidine tag, a c-myc tag and a V5 tag. The present disclosure also provides polynucleotides, proteins, vectors and host cells that comprise the triple tag sequence of the present disclosure, including libraries of such polynucleotides, proteins, vectors and host cells. The novel triple tag sequences of the present disclosure may be used in phage display vectors and phage libraries and in methods for detection, screening, capture, purification, quantitation, and/or recovery of proteins of interest to which they are linked. Proteins of interest include antibodies such as single chain antibodies, single chain antibodies, and Fab fragments of antibodies or peptides such as non-antibody peptides.

1 Claim, 11 Drawing Sheets

(56) References Cited

OTHER PUBLICATIONS

International Report on Patentability for International Application No. PCT/US2009/059408, dated Apr. 14, 2011.
International Search Report for International Application No. PCT/US2009/059408, dated Mar. 5, 2010.
Jarvik et al. Annu Rev Genet. (1998) 32:601-618.
Khatri et al. Biochem J. (2004) 378:207-212 "Evidence for a second peptide cleavage in the C-terminal domain of rodent intestinal mucin Muc3".
Krebber et al. J. Immunological Methods (1997) 201:35-55 Reliable cloning of functional antibody variable domains from hybridomas and spleen cell repertoires employing a reengineered phage display system.
Schofield et al. (2007) Genome Biology, 8:R254.-R254.18.
Wang et al. Biochem J. (2002 366:623-631 "C-terminal domain of rodent intestinal mucin Muc3 is proteolytically cleaved in the endoplasmic reticulum to generate extracellular and membrane components".

* cited by examiner

SEQUENCE LISTING

```
<160> NUMBER OF SEQ ID NOS: 18

<210> SEQ ID NO 1
<211> LENGTH: 6
<212> TYPE: PRT
<213> ORGANISM: Artificial
<220> FEATURE:
<223> OTHER INFORMATION: Synthesized: 6X Histidine Tag

<400> SEQUENCE: 1

His His His His His His
```

```
<210> SEQ ID NO 2
<211> LENGTH: 10
<212> TYPE: PRT
<213> ORGANISM: Artificial
<220> FEATURE:
<223> OTHER INFORMATION: Synthesized: C-myc tag

<400> SEQUENCE: 2

Glu Gln Lys Leu Ile Ser Glu Glu Asp Leu
1               5                   10

<210> SEQ ID NO 3
<211> LENGTH: 14
<212> TYPE: PRT
<213> ORGANISM: Artificial
<220> FEATURE:
<223> OTHER INFORMATION: Synthesized: V5 tag

<400> SEQUENCE: 3

Gly Lys Pro Ile Pro Asn Pro Leu Leu Gly Leu Asp Ser Thr
1               5                   10

<210> SEQ ID NO 4
<211> LENGTH: 30
<212> TYPE: PRT
<213> ORGANISM: Artificial
<220> FEATURE:
<223> OTHER INFORMATION: Synthesized: Triple tag (HMV)

<400> SEQUENCE: 4

His His His His His His Glu Gln Lys Leu Ile Ser Glu Glu Asp Leu
1               5                   10                  15

Gly Lys Pro Ile Pro Asn Pro Leu Leu Gly Leu Asp Ser Thr
            20                  25                  30

<210> SEQ ID NO 5
<211> LENGTH: 36
<212> TYPE: PRT
<213> ORGANISM: Artificial
<220> FEATURE:
<223> OTHER INFORMATION: Synthesized: Triple tag (HMV) with spacers

<400> SEQUENCE: 5

His His His His His His Gly Ala Ala Glu Gln Lys Leu Ile Ser Glu
1               5                   10                  15

Glu Asp Leu Lys Ala Ala Gly Lys Pro Ile Pro Asn Pro Leu Leu Gly
            20                  25                  30

Leu Asp Ser Thr
        35

<210> SEQ ID NO 6
<211> LENGTH: 18
<212> TYPE: PRT
<213> ORGANISM: Artificial
<220> FEATURE:
<223> OTHER INFORMATION: Synthesized: Linker sequence

<400> SEQUENCE: 6

Ala Ser Thr Gly Gly Gly Gly Ser Gly Gly Gly Gly Ser Gly Gly Gly
1               5                   10                  15

Gly Ser

<210> SEQ ID NO 7
```

```
<211> LENGTH: 22
<212> TYPE: PRT
<213> ORGANISM: Artificial
<220> FEATURE:
<223> OTHER INFORMATION: Synthesized: Pectate lyase signal sequence
      (PelB)

<400> SEQUENCE: 7

Met Lys Tyr Leu Leu Pro Thr Ala Ala Ala Gly Leu Leu Leu Leu Ala
1               5                   10                  15

Ala Gln Pro Ala Met Ala
            20

<210> SEQ ID NO 8
<211> LENGTH: 19
<212> TYPE: PRT
<213> ORGANISM: Artificial
<220> FEATURE:
<223> OTHER INFORMATION: Synthesized: Eukaryotic signal sequence 1

<400> SEQUENCE: 8

Met Lys Ile Leu Ile Leu Gly Ile Phe Leu Phe Leu Cys Ser Thr Pro
1               5                   10                  15

Ala Trp Ala

<210> SEQ ID NO 9
<211> LENGTH: 19
<212> TYPE: PRT
<213> ORGANISM: Artificial
<220> FEATURE:
<223> OTHER INFORMATION: Synthesized: Eukaryotic signal sequence 2

<400> SEQUENCE: 9

Met Arg Thr Leu Ala Ile Leu Ala Ala Ile Leu Leu Val Ala Leu Gln
1               5                   10                  15

Ala Gln Ala

<210> SEQ ID NO 10
<211> LENGTH: 21
<212> TYPE: PRT
<213> ORGANISM: Artificial
<220> FEATURE:
<223> OTHER INFORMATION: Synthesized: Eukaryotic signal sequence 3

<400> SEQUENCE: 10

Met Gly Ala Leu Ala Val Phe Ala Val Ala Cys Leu Ala Ala Val Ala
1               5                   10                  15

Ser Val Ala His Ala
            20

<210> SEQ ID NO 11
<211> LENGTH: 60
<212> TYPE: DNA
<213> ORGANISM: Artificial
<220> FEATURE:
<223> OTHER INFORMATION: Synthesized: RLMycLinkV5R1 primer

<400> SEQUENCE: 11
gttagggata ggcttacctg cggccccatt cagatcctct tctgagatga gttttgttc        60

<210> SEQ ID NO 12
<211> LENGTH: 54
<212> TYPE: DNA
<213> ORGANISM: Artificial
<220> FEATURE:
<223> OTHER INFORMATION: Synthesized: RLLinkV5R2 primer
```

```
<400> SEQUENCE: 12
cgtagaatcg agaccgagga gagggttagg gataggctta cctgcggccc catt        54

<210> SEQ ID NO 13
<211> LENGTH: 59
<212> TYPE: DNA
<213> ORGANISM: Artificial
<220> FEATURE:
<223> OTHER INFORMATION: Synthesized: RLV5For primer

<400> SEQUENCE: 13
cctaaccctc tcctcggtct cgattctacg aatggggccg cataggaggc tagttctgc   59

<210> SEQ ID NO 14
<211> LENGTH: 25
<212> TYPE: DNA
<213> ORGANISM: Artificial
<220> FEATURE:
<223> OTHER INFORMATION: Synthesized: IR26 (For)primer

<400> SEQUENCE: 14
gagtgcgacg gcctcgagcc cgccc                                        25

<210> SEQ ID NO 15
<211> LENGTH: 25
<212> TYPE: DNA
<213> ORGANISM: Artificial
<220> FEATURE:
<223> OTHER INFORMATION: Synthesized: IR30 (Rev)primer

<400> SEQUENCE: 15
caatagaaaa ttcatatggt ttacc                                        25

<210> SEQ ID NO 16
<211> LENGTH: 40
<212> TYPE: DNA
<213> ORGANISM: Artificial
<220> FEATURE:
<223> OTHER INFORMATION: Synthesized: IL28Sfi_For primer

<400> SEQUENCE: 16
taattactcg cggcccagcc ggccatggcc caggtccagc                        40

<210> SEQ ID NO 17
<211> LENGTH: 43
<212> TYPE: DNA
<213> ORGANISM: Artificial
<220> FEATURE:
<223> OTHER INFORMATION: Synthesized: IL28Sfi_Rev primer

<400> SEQUENCE: 17
tatataatat ggccccccgag gccgacataa gaactcaggc cgc                   43

<210> SEQ ID NO 18
<211> LENGTH: 152
<212> TYPE: PRT
<213> ORGANISM: Artificial
<220> FEATURE:
<223> OTHER INFORMATION: Synthesized: PIII (TRUNCATED)

<400> SEQUENCE: 18

Ser Gly Asp Phe Asp Tyr Glu Lys Met Ala Asn Ala Asn Lys Gly Ala
1               5                   10                  15

Met Thr Glu Asn Ala Asp Glu Asn Ala Leu Gln Ser Asp Ala Lys Gly
            20                  25                  30
```

```
Lys Leu Asp Ser Val Ala Thr Asp Tyr Gly Ala Ala Ile Asp Gly Phe
         35                  40                  45

Ile Gly Asp Val Ser Gly Leu Ala Asn Gly Asn Gly Ala Thr Gly Asp
 50                  55                  60

Phe Ala Gly Ser Asn Ser Gln Met Ala Gln Val Gly Asp Gly Asp Asn
 65              70                  75                      80

Ser Pro Leu Met Asn Asn Phe Arg Gln Tyr Leu Pro Ser Leu Pro Gln
             85                  90                  95

Ser Val Glu Cys Arg Pro Phe Val Phe Ser Ala Gly Lys Pro Tyr Glu
            100                 105                 110

Phe Ser Ile Asp Cys Asp Lys Ile Asn Leu Phe Arg Gly Val Phe Ala
        115                 120                 125

Phe Leu Leu Tyr Val Ala Thr Phe Met Tyr Val Phe Ser Thr Phe Ala
        130                 135                 140

Asn Ile Leu Arg Asn Lys Glu Ser
145                 150
```

US 8,546,307 B2

TRIPLE TAG SEQUENCE AND METHODS OF USE THEREOF

FIELD

The present disclosure relates to novel triple tag sequences. The novel tag sequences may comprise a 6× histidine tag, a c-myc tag and a V5 tag, wherein the c-myc tag is positioned between the 6× histidine tag and V5 tag. Polynucleotides, proteins, vectors and host cells that comprise a triple tag sequence are also provided by the present disclosure including, libraries of such polynucleotides, proteins, vectors and host cells. The novel triple tag sequences of the present disclosure may be used in phage display vectors and phage libraries and in methods for detection, screening, capture, purification, quantitation, and/or recovery of proteins of interest to which they are linked. Proteins of interest include antibody molecules such as single chain antibodies (e.g., scFv), single domain antibodies (e.g., $V_H$, $V_L$) and Fab fragments of antibodies.

BACKGROUND

Epitope tags are short peptide sequences which can make a gene product immunoreactive to an already existing antibody and thus allow for detection, capture or purification of the gene product (Jarvik and Telmer (1998) *Annu. Rev. Genet.* 32:601-618). Such tags (e.g., V5, derived from a small epitope present on the P and V proteins of the paramyxovirus; c-myc, derived from a leucine zipper motif in human c-myc; and/or HA, derived from an influenza virus hemagglutinin peptide) may be derived from viral genes leading to their high immunoreactivity. Epitope tagging typically involves inserting the nucleotide sequence encoding the tag amino acid sequence into a gene of interest in frame with the coding region and expressing the gene in an appropriate host so that the tag amino acids are incorporated into the protein of interest. The tagged protein can then be detected, immobilized and/or purified by virtue of the tag's interaction with an antibody specific to the epitope tag. This approach can be used to elucidate the size of the tagged protein as well as its abundance, cellular location, posttranslational modifications and interactions with other proteins. In particular, antibodies recognizing a tag sequence facilitate detection, purification and/or isolation of tagged proteins.

Tagged proteins may include, for example, antibody molecules including antibody fragments, such as single chain antibodies (e.g., scFvs) and Fab fragments that lack a portion or all of the antibody constant domains normally found in an intact antibody. Both scFvs and Fab fragments have been successfully displayed on the surface of viruses and cells such as bacteriophage and bacterial or yeast cells, which has allowed for the selection of antibody fragments with antigen binding affinities as high as their divalent counterparts. Evaluation of antibodies is greatly facilitated by immobilization or capture of the antibody and analysis of its interaction with other proteins. Full-length IgGs may be captured through their Fc region using an anti-Fc antibody or by binding to proteins such as Protein A, Protein G, Protein NG or other antibody binding proteins. However, the lack of an Fc domain in some antibody fragments, such as single chain antibodies (e.g., ScFv) or single domain antibodies (e.g., dAb), precludes the use of an Fc capture reagent. While Fab fragments contain a CH1/CL constant region, this domain varies between different subclasses of antibodies and this does not provide a region that allows consistent capture with single Fc capture reagent. In addition, capturing with anti-Fab antibodies may interfere with binding of the antibody to its antigen. As such, tag sequences have been employed to capture antibody binding fragments that lack an Fc region in whole or in part.

SUMMARY

The present disclosure relates to novel triple tag sequences. The present disclosure provides polynucleotides, proteins, vectors and host cells that comprise or encode the novel triple tag sequences, including libraries of such polynucleotides, proteins, vectors and host cells.

The present disclosure provides vectors comprising a polynucleotide coding for a protein of interest linked to a polynucleotide coding for a triple tag sequence, wherein the triple tag sequence comprises 6× histidine (HHHHHH SEQ ID NO: 1), c-myc (EQKLISEEDL SEQ. ID NO: 2) and V5 (GKPIP-NPLLGLDST SEQ ID NO: 3), including wherein a c-myc tag is positioned between a 6× histidine tag and a V5 tag. In some embodiments, the protein of interest is an antibody, for example, a single chain antibody, single domain antibody or Fab. In some embodiments, the protein of interest is a peptide, for example, a non-antibody peptide.

In some embodiments, the 6× histidine (SEQ ID NO: 1), c-myc (SEQ ID NO: 2) and V5 (SEQ ID NO: 3) are directly linked. In some embodiments, the 6× histidine (SEQ ID NO: 1), c-myc (SEQ ID NO: 2) and V5 (SEQ ID NO: 3) are indirectly linked through one or more spacers. In some embodiments, the spacer is 3 to 7 amino acids in length. In some embodiments, the spacer is GAA or KAA.

In some embodiments, the polynucleotide codes for a triple tag sequence that is represented by HHHHHHEQKLISEED-LGKPIPNPLLGLDST (SEQ ID NO: 4). In some embodiments, the polynucleotide codes for a triple tag sequence that is represented by HHHHHHGAAEQKLISEEDLKAAGK-PIPNPLLGLDST (SEQ ID NO: 5). In some embodiments, the polynucleotide coding for a triple tag sequence is a polynucleotide that codes for a triple tag sequence that is 90% identical to SEQ ID NO: 4 or SEQ ID NO: 5, a polynucleotide that hybridizes under stringent conditions to a polynucleotide that codes for a triple tag sequence that is SEQ ID NO: 4 or SEQ ID NO: 5, or a polynucleotide that codes for a triple tag sequence that is complementary to SEQ ID NO: 4 or SEQ ID NO: 5.

In some embodiments, a polynucleotide coding for a protein of interest and/or a polynucleotide coding for a triple tag sequence is operably linked to one or more expression control elements. In some embodiments, the expression control element is a promoter. In some embodiments, the promoter is a bacterial or yeast promoter.

In some embodiments, a polynucleotide coding for a protein of interest, (e.g., a single chain antibody) and/or a polynucleotide coding for a triple tag sequence is operably linked to a polynucleotide coding for a signal sequence selected from the group consisting of: MKYLLPTAAAGLLLLAAQ-PAMA (SEQ ID NO: 7), MKILILGIFLFLCSTPAWA (SEQ ID NO: 8), MRTLAILAAILLVALQAQA (SEQ ID NO: 9), and MGALAVFAVACLAAVASVAHA (SEQ ID NO: 10).

In some embodiments, the polynucleotide coding for a protein of interest codes for a binding molecule or fragment thereof. In some embodiments, the binding molecule is an antibody or fragment thereof. In some embodiments, the antibody or binding fragment thereof is selected from the group consisting of Fab, Fab', Fab'-SH, Fv, scFv, and a F(ab')$_2$. In some embodiments, the antibody or binding fragment thereof is a single chain antibody (e.g. scFV), or a single domain antibody (e.g., dAb). In some embodiments, the 5' end of the polynucleotide coding for the triple tag sequence is operably linked to the 3' end of the polynucleotide coding for a protein of interest. In some embodiments, the 3' end of the polynucleotide coding for the triple tag sequence is operably linked to the 5' end of the polynucleotide coding for a protein of interest.

Host cells are also provided that comprise vectors or polynucleotides of the present disclosure, including libraries of such host cells.

The present disclosure also provides methods of producing a protein of interest operably linked to a triple tag sequence comprising culturing a host cell of the present disclosure under conditions wherein a polynucleotide sequence encoding such a protein is expressed and a protein of interest linked to a triple tag sequence (e.g., a tagged protein) is produced. In some embodiments, the methods further comprise detecting, capturing and/or recovering a protein from a host cell, including a host cell culture.

The present disclosure also provides tagged proteins that comprise a protein of interest for example, a single chain antibody or a peptide, linked to a triple tag sequence comprising 6× histidine (SEQ ID NO: 1), c-myc (SEQ ID NO: 2) and V5 (SEQ ID NO: 3).

In some embodiments, the 6× histidine (SEQ ID NO: 1), c-myc (SEQ ID NO: 2) and V5 (SEQ ID NO: 3) are directly linked. In some embodiments, the 6× histidine (SEQ ID NO: 1), c-myc (SEQ ID NO: 2) and V5 (SEQ ID NO: 3) are indirectly linked through one or more spacers. In some embodiments, the spacer is 3 to 7 amino acids in length. In some embodiments, the spacer is GAA or KAA.

In some embodiments, a triple tag sequence is represented by HHHHHHEQKLISEEDLGKPIPNPLLGLDST (SEQ ID NO: 4). In some embodiments, a triple tag sequence is represented by HHHHHHGAAEQKLISEEDLKAAGKPIPNPLLGLDST (SEQ ID NO: 5). In some embodiments, the triple tag sequence is 70% identical to SEQ ID NO: 4 or SEQ ID NO: 5. In some embodiments, the triple tag sequence is 80% identical to SEQ ID NO: 4 or SEQ ID NO: 5. In some embodiments, the triple tag sequence is 90% identical to SEQ ID NO: 4 or SEQ ID NO: 5.

The present disclosure provides methods for detection, capture and/or recovery of proteins of interest. Such methods include use of replicable genetic packages (e.g., cells or viruses) that comprise polynucleotides that code for proteins of interest linked to a triple tag sequence (e.g., tagged proteins). Libraries of replicable genetic packages, including, for example, viruses or cells such as bacteriophage and bacterial or yeast cells, displaying tagged proteins of the present disclosure on their surface, may be used for detection (e.g., for screening or selection) capture (e.g., for quantitation or affinity based screening) and or recovery (e.g., purification) of the proteins of interest (e.g., antibodies such as a single chain antibody, single domain antibody or Fab).

In some embodiments, the methods for detection are methods of detecting a tagged protein by contacting a replicable genetic package (e.g., virus or cell such as a bacteriophage, bacterial cell, or yeast cell or a ribosome) or an extract of a replicable genetic package (e.g., an extract from a cell, including a cell culture, such as a periplasmic extract from bacterial cells) with an antibody to 6× histidine (e.g., SEQ ID NO: 1), an antibody to c-myc (e.g., SEQ ID NO: 2) and/or an antibody to V5 (e.g., SEQ ID NO: 3), wherein the tagged protein is detected by the antibody to 6× histidine, the antibody to c-myc and/or the antibody to V5. Such an antibody includes those that to bind to the tag and have a $k_{off}$ of about $10^{-2}$ and preferably about $10^{-3}$ or less (e.g., slower off rate).

In some embodiments, the methods for capture are methods of capturing a tagged protein by contacting a replicable genetic package (e.g., virus or cell such as a bacteriophage, bacterial cell, or yeast cell or a ribosome) or an extract of a replicable genetic package (e.g., an extract from a cell, including a cell culture, such as a periplasmic extract from bacterial cells) with an antibody to 6× histidine (e.g., SEQ ID NO: 1), an antibody to c-myc (e.g., SEQ ID NO: 2) and/or and antibody to V5 (e.g., SEQ ID No: 3), wherein the tagged protein is bound to the antibody to 6× histidine, the antibody to c-myc and/or the antibody to V5. Such a capture antibody includes those that bind to the tag with a $k_{off}$ of about $10^{-4}$ and preferably about $10^{-6}$, $10^{-6}$ or less (e.g., slower off rate).

In some embodiments, the methods for recovery are methods of recovering (e.g., obtaining) a tagged protein or one or more replicable genetic packages (e.g., viruses or cells) expressing a protein of interest, including, for example a binding molecule or fragment thereof such as an antibody or a protein specific for a binding partner, from an extract by expressing a protein of interest operably linked to a triple tag sequence that comprises 6× histidine (SEQ ID NO: 1), c-myc (SEQ ID NO: 2) and V5 (SEQ ID NO: 3); screening the replicable genetic packages for binding to antibodies specific for 6× histidine (SEQ ID NO: 1), c-myc (SEQ ID NO: 2) and/or V5 (SEQ ID NO: 3); and obtaining tagged proteins or detecting, capturing and/or recovering replicable genetic packages that bind to one or more of the antibodies.

Libraries of replicable genetic packages, including for example, viruses or cells such as bacteriophage, bacterial cells or yeast cells or ribosomes, displaying on their surface tagged proteins of the present disclosure are provided. Tagged proteins of the present disclosure comprise an amino acid sequence of a protein of interest (e.g., an antibody such as a single chain antibody or a peptide such as a non-antibody peptide) and a triple tag sequence (e.g., comprising 6× histidine (SEQ ID NO: 1), c-myc (SEQ ID NO: 2) and V5 (SEQ ID NO. 3) that are directly linked (e.g., SEQ ID NO 4) or indirectly linked through one or more spacers (e.g., SEQ ID NO: 5).

Nucleic acid libraries comprising a plurality of tagged polynucleotides of the present disclosure are provided. Tagged polynucleotides of the present disclosure code for tagged proteins which comprise an amino acid sequence of a protein of interest (e.g., an antibody such as a single chain antibody or a peptide such as a non-antibody peptide) and a triple tag sequence (e.g., comprising 6× histidine (SEQ ID NO: 1), c-myc (SEQ ID NO: 2) and V5 (SEQ ID NO: 3) that are directly linked (e.g., SEQ ID NO 4) or indirectly linked through one or more spacers (e.g., SEQ ID NO: 5).

The present disclosure also provides methods of capturing a tagged protein by preparing a cell extract, such as a bacterial cell periplasmic extract, from the host cell expressing a tagged protein of the present disclosure; and contacting the cell extract, such as a bacterial cell periplasmic extract, with an antibody to 6× histidine, c-myc or V5, wherein the tagged protein is captured by the antibody to 6× histidine, c-myc and/or V5.

The present disclosure also provides methods for recovering a tagged protein by preparing a cell extract, such as a bacterial cell periplasmic extract, from the host cell of the present disclosure; contacting the periplasmic extract with an antibody or a matrix such as a metal chelating or other matrix (e.g., a nickel column) that binds a 6× histidine tag, c-myc tag and/or V5 tag, wherein the tagged protein binds to an antibody or a matrix such as a metal chelating or other matrix (e.g., a nickel column) that binds the 6× histidine tag, c-myc tag and/or V5 tag; eluting tagged protein bound to the antibody or matrix (e.g., a nickel column for the 6× histidine tag); and recovering the tagged protein from the eluate.

The present disclosure also provides methods of screening a phagemid library of proteins by expressing a plurality of polynucleotides of the present disclosure (e.g., polynucleotides coding for a protein of interest linked to a polynucleotide coding for a triple tag sequence); screening the expressed proteins (e.g., tagged proteins comprising proteins of interest and triple tags) for binding to an antibody specific for V5, c-myc or 6× histidine; and recovering the expressed proteins that are bound.

The present disclosure provides vectors comprising a polynucleotide comprising a DNA sequence coding for a single chain antibody linked at its 3' end to a sequence coding for a triple tag sequence as represented by SEQ ID NO: 5 (HHH-HHHGAAEQKLISEEDLKAAGKPIPNPLLGLDST).

In some embodiments, the DNA sequence coding for a single chain antibody and/or DNA sequence coding for a triple tag sequence is operably linked to one or more expression control elements. In some embodiments, the expression control element is a promoter, such as a bacterial or yeast promoter.

In some embodiments, a DNA sequence coding for a signal sequence as represented by MKYLLPTAAAGLLLLAAQ-PAMA (SEQ ID NO: 7) is linked at its 3' end to a DNA sequence coding for a protein of interest, for example, a single chain antibody. Alternative signal sequences include MKIL-ILGIFLFLCSTPAWA (SEQ ID NO: 8), MRTLAIL-AAILLVALQAQA (SEQ ID NO: 9) or MGALAVFAVAC-LAAVASVAHA (SEQ ID NO: 10).

Host cells are also provided that comprise vectors or polynucleotides of the present disclosure, including wherein the host cell was transfected or transformed with the vectors or polynucleotides and wherein the vectors or polynucleotides code for a protein of interest such as an antibody (e.g., single chain antibody, single domain antibody or Fab) or a peptide (e.g., a non-antibody peptide) and a triple tag that comprises 6× histidine, c-myc and V5 sequences or that is SEQ ID NO: 4 or SEQ ID NO: 5.

The present disclosure also provides methods of producing a single chain antibody linked to a triple tag sequence comprising culturing a host cell of the present disclosure under conditions wherein a polynucleotide sequence coding for such a single chain antibody is expressed and a single chain antibody linked to a triple tag sequence is produced. In some embodiments, the methods further comprise recovering the protein (e.g., single chain antibody with or without the triple tag sequence) from a host cell such as a host cell culture.

The present disclosure also provides a tagged protein that is a single chain antibody, a single domain antibody or a Fab linked to triple tag sequence as represented by SEQ ID NO: 5 (HHHHHHGAAEQKLISEEDLKAAGKPIPN-PLLGLDST), wherein the triple tag sequence is linked to the C-terminus of the single chain antibody. Such tagged proteins may be expressed from a library of polynucleotides or from a library of replicable genetic packages such as cells (e.g., bacterial or yeast) or viruses (e.g., bacteriophage) or ribosomes and may be detected, captured and/or recovered.

In some embodiments, the triple tag sequence is directly linked to the C-terminus of the single chain antibody. In some embodiments, the triple tag sequence is linked to the C-terminus of the single chain antibody through a spacer.

Libraries of bacteriophage displaying on their surface the tagged protein of the present disclosure are provided as well as methods for detecting, capturing and/or recovering the bacteriophage and/or the tagged protein from the libraries.

Nucleic acid libraries comprising a plurality of polynucleotides (e.g., coding for a protein of interest such as an antibody, single chain antibody, single domain antibody or Fab) operably linked to a triple tag sequence comprising 6× histidine, c-myc and V5 sequences (e.g., SEQ ID NO: 4 or SEQ ID NO: 5) of the present disclosure are provided.

The present disclosure provides methods of capturing a tagged single chain antibody (e.g., comprising 6× histidine, c-myc and V5 sequences such as SEQ ID NO: 4 or SEQ ID NO: 5) by preparing a periplasmic extract from the host cell of the present disclosure; and contacting the periplasmic extract with an antibody to V5 (or alternatively to c-myc or 6× histidine), wherein the tagged single chain antibody is captured by the antibody to V5 (or alternatively to c-myc or 6× histidine). Optionally the captured tagged single chain antibody can be detected and/or quantitated using an antibody to 6× histidine, c-myc or V5 wherein the antibody to detect and/or quantify is different from the antibody to capture.

The present disclosure also provides methods for recovering a tagged single chain antibody (e.g., comprising 6× histidine, c-myc and V5 sequences such as SEQ ID NO: 4 or SEQ ID NO: 5) by preparing a periplasmic extract from the host cell of the present disclosure; contacting the periplasmic extract with a metal chelating matrix such as a nickel column, wherein the tagged single chain antibody binds to the matrix such as a nickel column; eluting tagged single chain antibody bound to the matrix such as the column; and recovering the tagged single chain antibody from the eluate.

The present disclosure also provides methods of screening a phagemid library of single chain antibodies (e.g., comprising 6× histidine, c-myc and V5 sequences such as SEQ ID NO: 4 or SEQ ID NO: 5) by expressing a plurality of polynucleotides of the present disclosure; screening the expressed polynucleotides for binding to an antibody specific for V5, c-myc or 6× histidine; and recovering the expressed polynucleotides that are bound.

Additional features and advantages are described herein, and will be apparent from, the following Detailed Description and the Figures.

DETAILED DESCRIPTION

Figure 1:
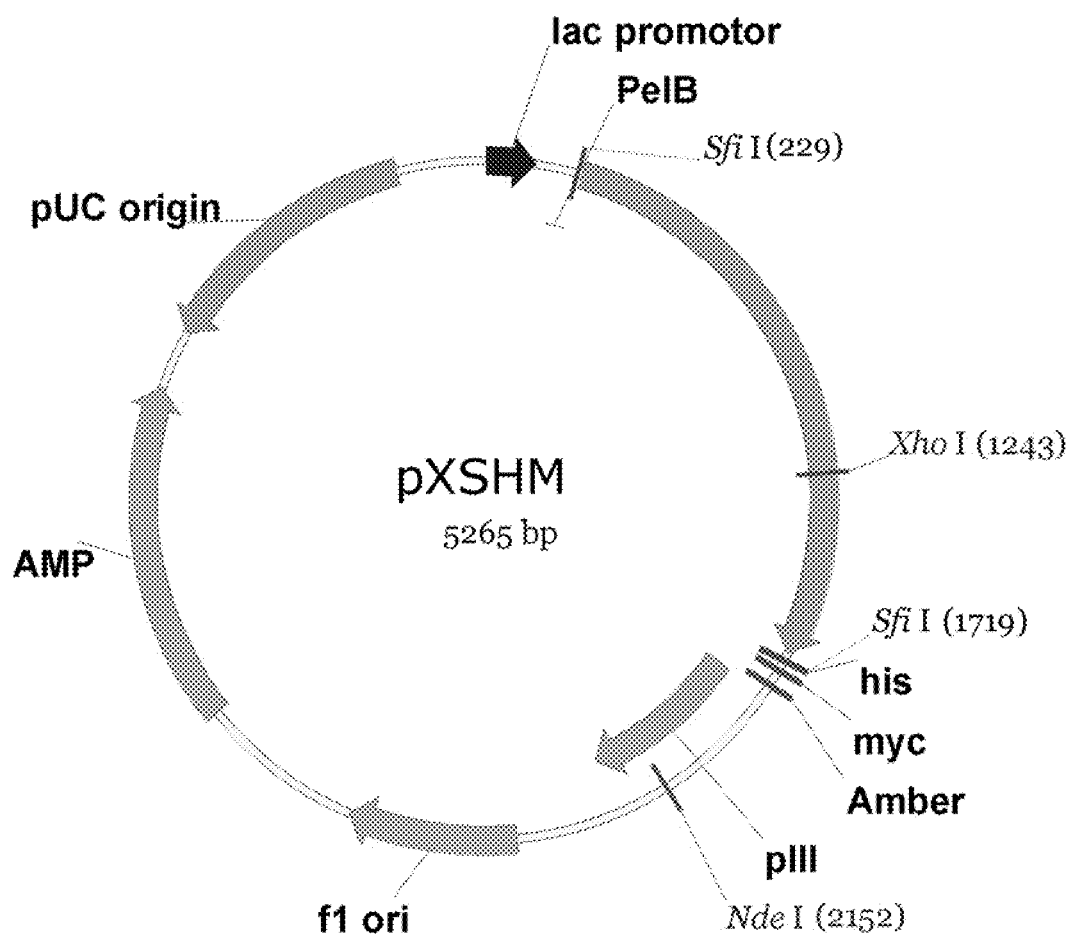
FIG. 1 shows a vector map for pXSHM.
Figure 2:
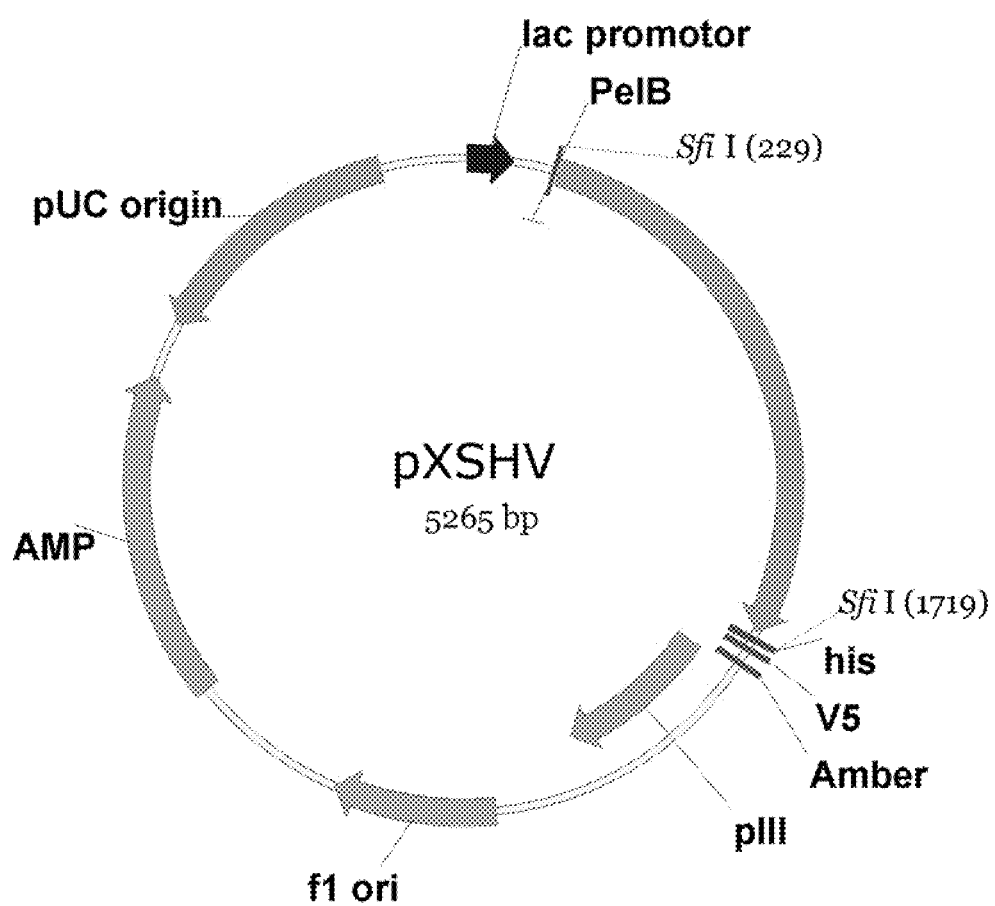
FIG. 2 shows a vector map for pXSHV.
Figure 3:
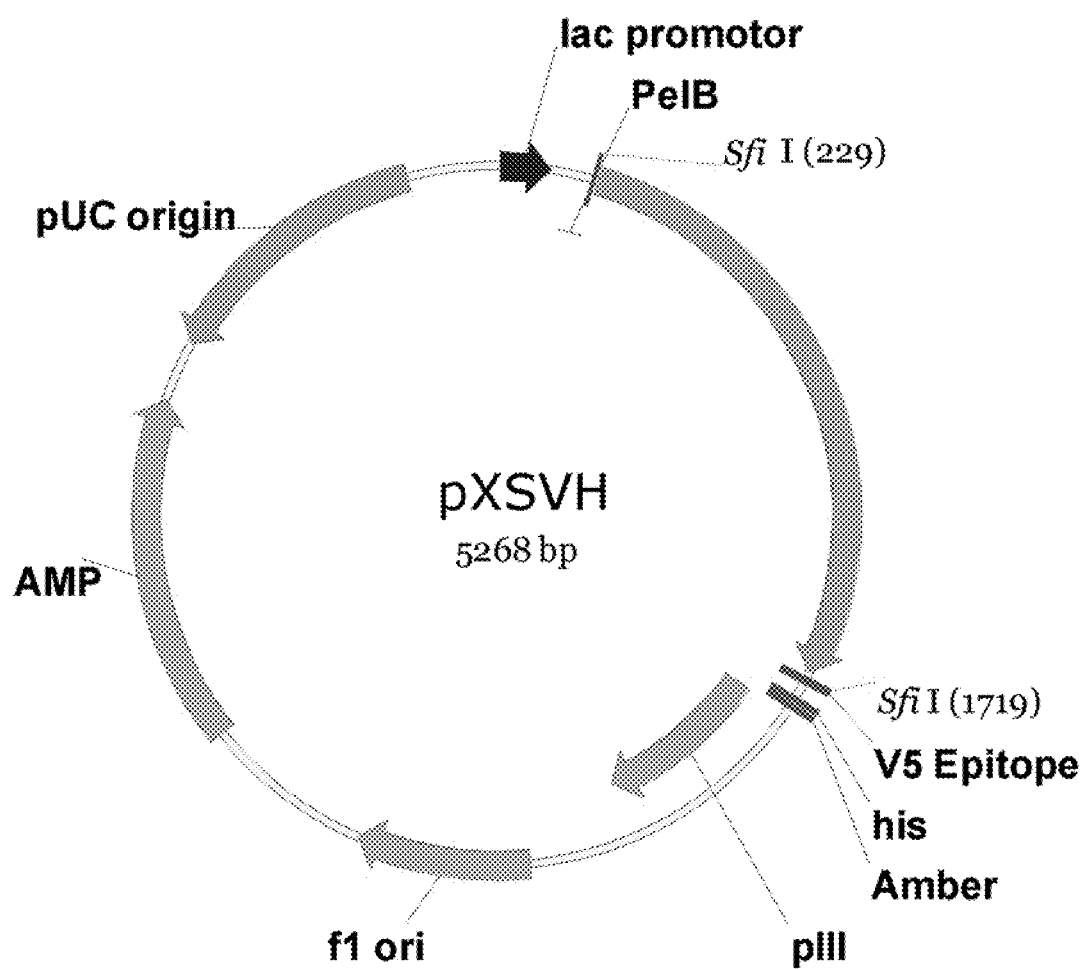
FIG. 3 shows a vector map for pXSVH.
Figure 4:
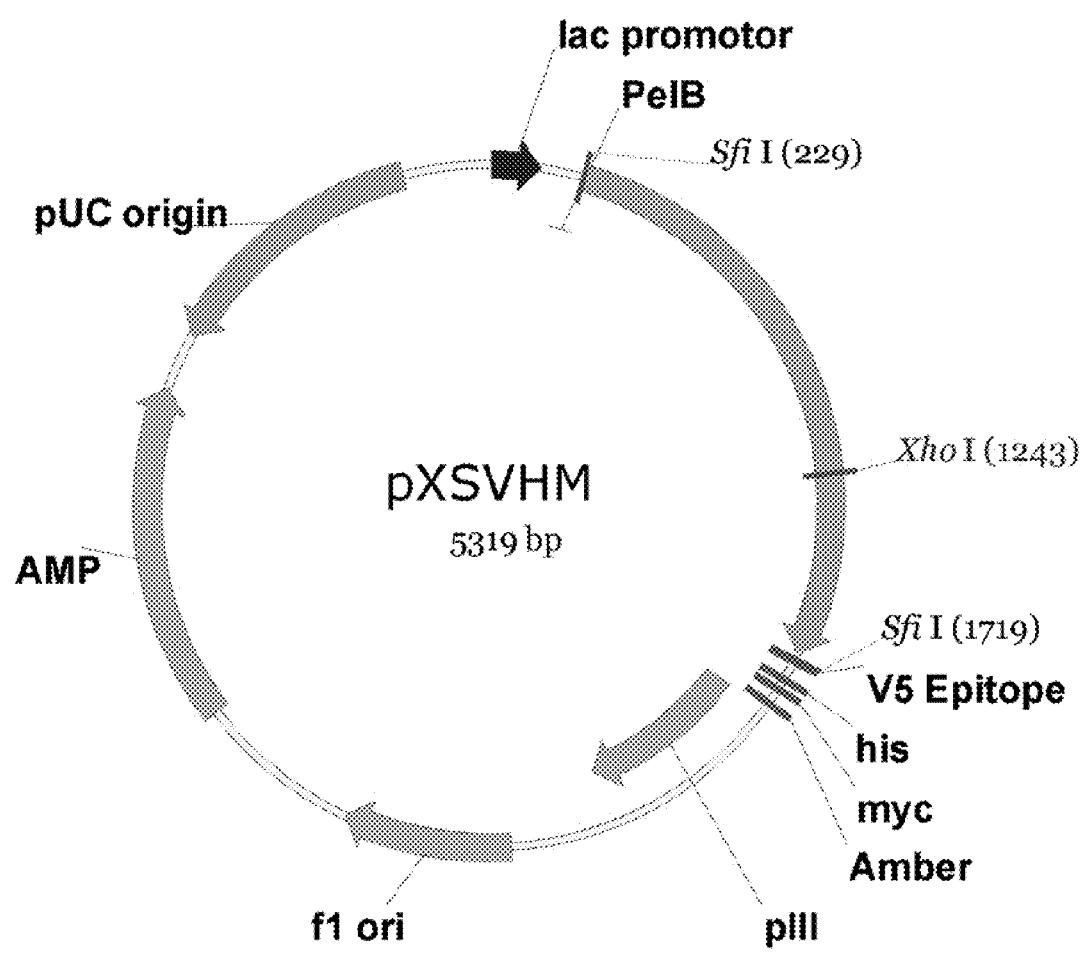
FIG. 4 shows a vector map for pXSVHM.
Figure 5:
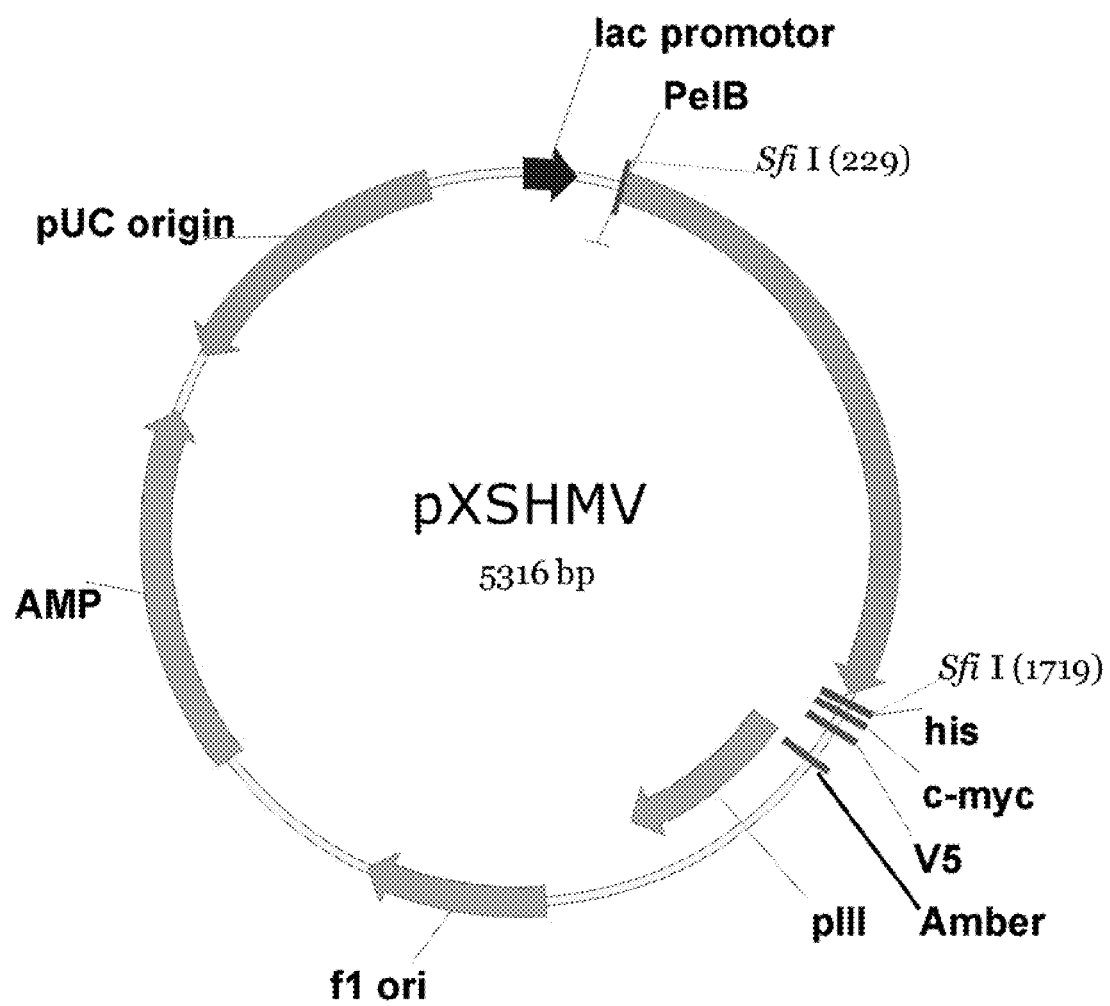
FIG. 5 shows a vector map for pXSHMV.

The present disclosure provides novel triple tag sequences. Numerous tags are known in the art and may be used in combination for the detection and/or purification of a protein to which the tag is linked (e.g., a tagged protein). However, when used in combination, one or more tags may be inaccessible to binding by an antibody due to the protein's secondary and/or tertiary structure and/or the tag(s) may alter (e.g., significantly decrease or block) the expression of the protein. In addition, the tags may alter the display of the protein in various libraries of tagged proteins and display systems including phage display library systems and/or may alter the stability of the display system such as a phage display library. Surprisingly, it has been discovered that a triple tag sequence comprising a 6× histidine tag (H or His) (e.g., SEQ ID NO: 1), a c-myc tag (M or Myc) (e.g., SEQ ID NO: 2) and a V5 tag (V or V5) (e.g., SEQ ID NO: 3) is able to bind an antibody to 6× histidine, an antibody to c-myc, and an antibody to V5, for example, when the triple tag sequence is linked to a protein of interest such as an antibody (e.g., single chain antibody, single domain antibody or Fab) or a peptide (e.g., a non-antibody peptide). Tagged proteins comprising a protein of interest linked to a triple tag sequence (e.g., with 6× histidine, c-myc and V5 sequences such as SEQ ID NO: 4 or SEQ ID NO: 5) may be detected (e.g., for screening or selection) captured (e.g., for quantitation or affinity based screening) and/or recovered (e.g., purified) according to methods as described herein, using antibodies to 6× histidine, c-myc, and/or V5. For detection, an antibody that binds to the 6× histidine tag, the c-myc tag or the V5 tag may be used. Such antibodies include those that bind to the tag (e.g., his, myc or V5) with a $k_{off}$ of about $10^{-2}$ and preferably about $10^{-3}$ or less (e.g., slower off rate). For capture, an antibody that stably binds to the 6× histidine tag, the c-myc tag or the V5 tag may be used and an antibody to V5 or 6× histidine is preferably used. Such antibodies include those that bind to the tag (e.g., V5, his or myc) with a $k_{off}$ of about $10^{-4}$, and preferably about $10^{-5}$ or about $10^{-6}$ or less (e.g., slower off rate). For recovery, for example, via purification, an antibody that binds to the 6× histidine tag, the c-myc tag or the V5 tag may be used. Preferably, the 6× histidine tag may be used and a matrix such as a metal chelating or other matrix (e.g., nickel or copper chelating resin) is used. Thus, all three tags are accessible and each is useful for detection, screening, capture, purification, quantitation and/or recovery of proteins of interest, including antibodies such as single chain antibodies, single domain antibodies and Fab fragments of antibodies as described herein. In addition, such a triple tag sequence surprisingly does not affect expression of the protein, for example an antibody such as a single chain antibody or a Fab. Further, such a triple tag sequence surprisingly does not alter the display of the protein in various libraries of tagged proteins (e.g., single chain antibodies and Fabs) and display systems including phage display library systems. Accordingly, in preferred embodiment, the c-myc tag is positioned between the 6× histidine and V5 tags (e.g., HHHHHHEQKLISEEDLGK-PIPNPLLGLDST (SEQ ID NO: 4)). The 6× histidine tag and/or V5 tag may be linked to the c-myc tag through a spacer sequence (e.g., HHHHHHGAAEQKLISEEDLKAAGKPIP-NPLLGLDST (SEQ ID NO: 5)). The spacer may comprise from 1 to 7 or more (e.g., 1, 2, 3, 4, 5, 6, 7 or more) amino acids (e.g., GAA or KAA). A novel triple tag sequence may be operably linked to one or more transcriptional units coding for one or more proteins of interest at either the 5' or 3' end of the transcription unit. Surprisingly, the dissociation rate of proteins linked to a novel triple tag sequence of the present disclosure is sufficiently slow to allow their use in affinity based screening, for example, using antibodies to 6× histidine, c-myc and/or V5. A novel triple tag sequence of the present disclosure may be used in methods to detect, capture, purify, recover and/or quantitate a protein of interest, including a single chain antibody (e.g., scFv), single domain antibody (e.g., $V_H$, $V_L$) or a Fab fragment of an antibody, for example, wherein the protein is linked to the triple tag sequence.

Nucleic Acids, Proteins, Vectors and Host Cells

The present disclosure provides a novel triple tag sequence that comprises a histidine tag (e.g., 6× histidine tag, such as the tag represented by SEQ ID NO: 1), a c-myc tag (e.g., SEQ ID NO: 2) and a V5 tag (e.g., SEQ ID NO: 3). The triple tag sequence may be a DNA sequence or an amino acid sequence.

The 6× histidine tag (SEQ ID NO: 1), c-myc tag (SEQ ID NO: 2) and V5 tag (SEQ ID NO: 3) may be directly linked. Alternatively, the 6× histidine tag (SEQ ID NO: 1), c-myc tag (SEQ ID NO: 2) and V5 tag (SEQ ID NO: 3) may be indirectly linked through a spacer. The spacer may be from 3 to 7 amino acids in length (e.g., GAA or KAA).

A triple tag DNA sequence may code for an amino acid sequence represented by HHHHHHEQKLISEEDLGKPIP-NPLLGLDST (SEQ ID NO: 4). Alternatively, a triple tag DNA sequence may code for an amino acid sequence represented by HHHHHHGAAEQKLISEEDLKAAGKPIPN-PLLGLDST (SEQ ID NO: 5). The DNA sequence coding for the triple tag sequence may be a DNA sequence that is 90% identical to SEQ ID NO: 4 or SEQ ID NO: 5, a DNA sequence that hybridizes under stringent conditions to a DNA sequence represented by SEQ ID NO: 4 or SEQ ID NO: 5, or a DNA sequence that is complementary to SEQ ID NO: 4 or SEQ ID NO: 5.

The triple tag sequence may be operably linked to the 5' end or the 3' end of a DNA sequence coding for a protein of interest. A protein of interest may include any known protein (e.g., an antibody molecule), peptide or fragment thereof. Antibody molecules include single chain antibodies (e.g., scFv), single domain antibodies (e.g., $V_H$, $V_L$) or Fab fragments of antibodies.

The triple tag sequence of the present disclosure may be linked to the C or N-terminus of a protein of interest. In some embodiments, the triple tag sequence is directly linked to the protein of interest. In other embodiment, the triple tag sequence is linked to the protein of interest through a linker. In some embodiments, the triple tag sequence is linked to an antibody (e.g., a single chain antibody, a single domain antibody or a Fab fragment). In embodiments where the protein of interest is a single chain antibody, it may comprise a linker (e.g., ASTGGGGSGGGGSGGGGS (SEQ ID NO: 6)) between the $V_H$ and $V_L$ domains. In some embodiments, a single chain antibody comprises 5' to 3', $V_H$-Linker-$V_L$ or $V_L$-Linker-$V_H$, wherein the linker is represented by ASTGGGGSGGGGSGGGGS (SEQ ID NO: 6).

In some embodiments, a triple tag sequence may be placed within the protein of interest (e.g., at a position interior from the C or N-terminus of the protein).

In some embodiments, a recognition site specific for a proteolytic enzyme (e.g., Xa or caspase-8) may be added near the triple tag sequence in the protein of interest, allowing recovery of the untagged protein.

Also provided are polypeptides and polynucleotides having 80-100%, including 81, 82, 83, 84, 85, 86, 87, 88, 89, 90, 91, 92, 93, 94, 95, 96, 97, 98 and 99%, sequence identity to SEQ ID NOS: 4 and 5, as well as nucleotides encoding any of these polypeptides, and complements of any of these nucleotides. Percent nucleic acid sequence identity refers to the percentage of nucleotides in a candidate sequence that are identical with the nucleotides in the triple tag sequence, after aligning the sequences and introducing gaps, if necessary, to achieve the maximum percent sequence identity. Alignment for purposes of determining percent nucleic acid sequence identity can be achieved in various ways that are within the skill in the art, for instance, using publicly available computer software such as BLAST, BLAST-2, ALIGN or Megalign (DNASTAR) software. Those skilled in the art can determine appropriate parameters for measuring alignment, including any algorithms needed to achieve maximal alignment over the full length of the sequences being compared.

Polynucleotides that hybridize under stringent conditions to the triple tag sequence of the present disclosure are also provided. The specificity of single stranded polynucleotide to hybridize complementary fragments is determined by the stringency of the reaction conditions. Hybridization stringency increases as the propensity to form DNA duplexes decreases. In nucleic acid hybridization reactions, the stringency can be chosen to either favor specific hybridizations (e.g., high stringency), which can be used to identify, for example, full-length clones from a library. Less-specific hybridizations (e.g., low stringency) can be used to identify related, but not exact, DNA molecules (e.g., homologous, but not identical) or segments.

DNA duplexes are stabilized by: (1) the number of complementary base pairs, (2) the type of base pairs, (3) salt concentration (ionic strength) of the reaction mixture, (4) the temperature of the reaction, and (5) the presence of certain organic solvents, such as formamide which decreases DNA duplex stability. In general, the longer the probe, the higher the temperature required for proper annealing. A common approach is to vary the temperature: higher relative temperatures result in more stringent reaction conditions.

To hybridize under stringent conditions describes hybridization protocols in which nucleotide sequences at least 60% homologous to each other remain hybridized. Generally, stringent conditions are selected to be about 5° C. lower than the thermal melting point (Tm) for the specific sequence at a defined ionic strength and pH.

Stringent hybridization conditions enable a probe, primer, polynucleotide or oligonucleotide to hybridize only to its target sequence. Stringent conditions are sequence-dependent and will differ. Stringent conditions comprise: (1) low ionic strength and high temperature washes (e.g. 15 mM sodium chloride, 1.5 mM sodium citrate, 0.1% sodium dodecyl sulfate at 50° C.); (2) a denaturing agent during hybridization (e.g. 50% (v/v) formamide, 0.1% bovine serum albumin, 0.1% Ficoll, 0.1% polyvinylpyrrolidone, 50 mM sodium phosphate buffer pH 6.5; 750 mM sodium chloride, 75 mM sodium citrate at 42° C.); or (3) 50% formamide. Washes typically also comprise 5×SSC (0.75 M NaCl, 75 mM sodium citrate), 50 mM sodium phosphate (pH 6.8), 0.1% sodium pyrophosphate, 5 times Denhardt's solution, sonicated salmon sperm DNA (50 μg/ml), 0.1% SDS, and 10% dextran sulfate at 42° C., with washes at 42° C. in 0.2 times SSC (sodium chloride/sodium citrate) and 50% formamide at 55° C., followed by a high-stringency wash consisting of 0.1× SSC containing EDTA at 55° C. Preferably, the conditions are such that sequences at least about 65%, 70%, 75%, 85%, 90%, 95%, 98%, or 99% homologous to each other typically remain hybridized to each other.

Changes may be introduced into a triple tag sequence that do not alter the function of the tag. For example, nucleotide substitutions leading to amino acid substitutions at "non-essential" amino acid residues may be made. A "non-essential" amino acid residue is a residue that can be altered from the wild-type sequences of the triple tag sequence without altering its biological activity, wherein the biological activity includes, for example, its ability to bind to an antibody to one of the tags (e.g., 6× histidine, c-myc or V5) in the triple tag sequence, whereas an "essential" amino acid residue is required for such biological activity. For example, amino acid residues that are conserved among the triple tag sequence of the disclosure are predicted to be particularly non-amenable to alteration. Amino acids for which conservative substitutions can be made are well known in the art.

A triple tag sequence may be inserted into a vector and used to transform a host cell. Exemplary methods for construction of a vector comprising a triple tag sequence of the present disclosure are provided below.

Many vectors are available, and selection of the appropriate vector may depend on: 1) whether it is to be used for DNA amplification or for expression of a polynucleotide of interest operably linked to a tag sequence, 2) the size of the DNA to be inserted into the vector, and 3) the host cell to be transformed with the vector. The vector components generally include, but are not limited to, one or more of the following: a signal sequence, an origin of replication, one or more marker genes, an enhancer element, a promoter, and a transcription termination sequence.

Tag sequences may include: HMV (6× histidine-c-myc-V5 or His-Myc-V5), VHM (V5-6× histidine-c-myc or V5-His-Myc), HV (6× histidine-V5 or His-V5), VH (V5-6× histidine or V5-His), and HM (6× histidine-c-myc or His-Myc).

For example, the cDNA or genomic DNA encoding a protein of interest linked to a triple tag sequence of the present disclosure may be inserted into a modified phage vector (e.g., phagemid). Construction of phage display libraries, including libraries constructed from phagemid vectors, exploits the bacteriophage's ability to display peptides and proteins on their surfaces, i.e., on their capsids. Often, filamentous phage such as M13, f1 or fd are used. Filamentous phage contain single-stranded DNA surrounded by multiple copies of genes encoding major and minor coat proteins, e.g., pIII. A protein of interest may be fused to a fragment of a coat protein, for example pIII. Fragments of pIII (e.g., pIII stump) may include the sequence represented by SEQ ID NO: 18. Phagemid vectors comprising sequence coding for pIII fragments such as SEQ ID NO: 18 may be used along with helper phage to construct a phage display library. Coat proteins are displayed on the capsid's outer surface. DNA sequences inserted in-frame with capsid protein genes are co-transcribed to generate fusion proteins or protein fragments displayed on the phage surface. Peptide phage libraries thus can display peptides representative of the diversity of the inserted genomic sequences. Significantly, these epitopes can be displayed in natural folded conformations. The peptides expressed on phage display libraries can then bind target molecules, i.e., they can specifically interact with binding partner molecules such as antibodies (Petersen (1995) *Mol. Gen. Genet.* 249: 425-31), cell surface receptors (Kay (1993) *Gene* 128:59-65), and extracellular and intracellular proteins (Gram (1993) *J. Immunol. Methods* 161:169-76).

The concept of using filamentous phages, such as M13, fd or fl, for displaying peptides on phage capsid surfaces was first introduced by Smith (1985) *Science* 228:1315-1317. Peptides have been displayed on phage surfaces to identify many potential ligands (see, e.g., Cwirla (1990) *Proc. Natl. Acad. ScL USA* 87:6378-6382). There are numerous systems and methods for generating phage display libraries described in the scientific and patent literature (see, e.g., Sambrook and Russell, Molecule Cloning: A Laboratory Manual, 3rd edition, Cold Spring Harbor Laboratory Press, Chapter 18, 2001; "Phage Display of Peptides and Proteins: A Laboratory Manual, Academic Press, San Diego, 1996; Crameri (1994) *Eur. J. Biochem.* 226:53-58; de Kruif (1995) *Proc. Natl. Acad. Sci. USA* 92:3938-42; McGregor (1996) *Mol. Biotechnol.* 6:155-162; Jacobsson (1996) *Biotechniques* 20:1070-1076;

Jespers (1996) *Gene* 173:179-181; Jacobsson (1997) *Microbiol Res.* 152:121-128; Fack (1997) *J. Immunol. Methods* 206:43-52; Rossenu (1997) *J. Protein Chem.* 16:499-503; Katz (1997) *Annu. Rev. Biophys. Biomol. Struct.* 26:27-45; Rader (1997) *Curr. Opin. Biotechnol.* 8:503-508; Griffiths (1998) *Curr. Opin. Biotechnol.* 9:102-108).

Typically, exogenous nucleic acid to be displayed are inserted into a coat protein gene, e.g. gene III or gene VIII of the phage. The resultant fusion proteins may be displayed on the surface of the capsid. Protein VIII is present in approximately 2700 copies per phage, compared to 3 to 5 copies for protein III. Multivalent expression vectors, such as phagemids, can be used for manipulation of exogenous genomic or antibody encoding inserts and production of phage particles in bacteria (see, e.g., Felici (1991) *J. Mol. Biol.* 222:301-310).

Phagemid vectors are often employed for constructing the phage library (e.g., phagemid vectors as shown in FIGS. 1-5). These vectors include the origin of DNA replication from the genome of a single-stranded filamentous bacteriophage, e.g., M13, f1 or fd. A phagemid can be used in the same way as an orthodox plasmid vector, but can also be used to produce filamentous bacteriophage particle that contain single-stranded copies of cloned segments of DNA. For example, T7 vectors can be employed in which the displayed product on the mature phage particle is released by cell lysis.

In addition to phage epitope display libraries, analogous epitope display libraries can also be used. For example, the methods of the disclosure can also use yeast surface displayed epitope libraries (see, e.g., Boder (1997) *Nat. Biotechnol.* 15:553-557), which can be constructed using such vectors as the pYD1 yeast expression vector. Other potential display systems include mammalian display vectors and *E. coli* libraries.

An antibody or antibody fragment, e.g., a scFv, Fab or Fv may be displayed on the surface of a phage using phage display techniques. Exemplary antibody phage display methods are known to those skilled in the art and are described, e.g., in Hoogenboom, *Overview of Antibody Phage-Display Technology and Its Applications*, from *Methods in Molecular Biology Antibody Phase Display: Methods and Protocols* (2002) 178:1-37 (O'Brien and Aitken, eds., Human Press, Totowa, N.J.). For example, a library of antibodies or antibody fragments (e.g., scFvs, Fabs, Fvs with an engineered intermolecular disulfide bond to stabilize the $V_H$-$V_L$ pair, and diabodies) can be displayed on the surface of a filamentous phage, such as the nonlytic filamentous phage fd or M13. Antibodies or antibody fragments with the desired binding specificity can then be selected.

An antibody phage-display library can be prepared using methods known to those skilled in the art (see, e.g., Hoogenboom, *Overview of Antibody Phage-Display Technology and Its Applications*, from *Methods in Molecular Biology: Antibody Phage Display: Methods and Protocols* (2002) 178:1-37 (O'Brien and Aitken, eds., Human Press, Totowa, N.J.).

In some embodiments, cDNA is cloned into a phage display vector, such as a phagemid vector (e.g., pCES1, pXOMA Fab or pXOMA Fab-gIII). Exemplary phagemid vectors are shown in FIGS. 1-5. In certain embodiments, cDNA encoding both heavy and light chains may be present on the same vector. In some embodiments, cDNA encoding scFvs are cloned in frame with all or a portion of gene III, which encodes the minor phage coat protein pIII. The phagemid directs the expression of the scFv-pIII fusion on the phage surface. In other embodiments, cDNA encoding heavy chain (or light chain) may be cloned in frame with all or a portion of gene III, and cDNA encoding light chain (or heavy chain) is cloned downstream of a signal sequence in the same vector. The signal sequence directs expression of the light chain or a portion thereof (e.g., a light chain variable region) (or heavy chain or portion thereof) into the periplasm of the host cell, where the heavy and light chains assemble into Fab fragments. Alternatively, in certain embodiments, cDNA encoding heavy chain and cDNA encoding light chain may be present on separate vectors. In certain embodiments, heavy chain and light chain cDNA may be cloned separately, one into a phagemid and the other into a phage vector, which both contain signals for in vivo recombination in the host cell.

The techniques for constructing and analyzing phage display libraries uses recombinant technology well known to those of skill in the art. General techniques, e.g., manipulation of nucleic encoding libraries, epitopes, antibodies, and vectors of interest, generating libraries, subcloning into expression vectors, labeling probes, sequencing DNA, DNA hybridization are described in the scientific and patent literature, see e.g., Sambrook and Russell, eds., Molecular Cloning: a Laboratory Manual (3rd), Vols. 1-3, Cold Spring Harbor Laboratory Press, (2001); Current Protocols in Molecular Biology, Ausubel, ed. John Wiley & Sons, Inc., New York (1997-2001); and, Laboratory Techniques in Biochemistry and Molecular Biology: Hybridization with Nucleic Acid Probes, Part I. Theory and Nucleic Acid Preparation, Tijssen, ed. Elsevier, N.Y. (1993). Sequencing methods typically use dideoxy sequencing, however, other methodologies are available and well known to those of skill in the art.

Viral promoters obtained from the genomes of viruses include promoters from polyoma virus, fowlpox virus, adenovirus (e.g., Adenovirus 2 or 5), herpes simplex virus (thymidine kinase promoter), bovine papilloma virus, avian sarcoma virus, cytomegalovirus, a retrovirus (e.g., MoMLV, or RSV LTR), Hepatitis-B virus, Myeloproliferative sarcoma virus promoter (MPSV), VISNA, and Simian Virus 40 (SV40). Heterologous mammalian promoters include, e.g., the actin promoter, immunoglobulin promoter, heat-shock protein promoters.

The early and late promoters of the SV40 virus are conveniently obtained as a restriction fragment that also contains the SV40 viral origin of replication (see, e.g., Fiers et al., *Nature*, 273:113 (1978); Mulligan and Berg, *Science*, 209:1422-1427 (1980); and Pavlakis et al., *Proc. Natl. Acad. Sci. USA*, 78:7398-7402 (1981)). The immediate early promoter of the human cytomegalovirus (CMV) is conveniently obtained as a Hind III E restriction fragment (see, e.g., Greenaway et al., *Gene*, 18:355-360 (1982)). A broad host range promoter, such as the SV40 early promoter or the Rous sarcoma virus LTR, is suitable for use in the present expression vectors.

Generally, a strong promoter is employed to provide for high level transcription and expression of the desired product. Among the eukaryotic promoters that have been identified as strong promoters for high-level expression are the SV40 early promoter, adenovirus major late promoter, mouse metallothionein-I promoter, Rous sarcoma virus long terminal repeat, and human cytomegalovirus immediate early promoter (CMV or CMV IE). In an embodiment, the promoter is a SV40 or a CMV early promoter.

The promoters employed can be constitutive or regulatable, e.g., inducible. Exemplary inducible promoters include jun, fos and metallothionein and heat shock promoters. One or both promoters of the transcription units can be an inducible promoter. In an embodiment, the GFP is expressed from a constitutive promoter while an inducible promoter drives transcription of the gene of interest and/or the amplifiable selectable marker.

The transcriptional regulatory region in higher eukaryotes may comprise an enhancer sequence. Many enhancer sequences from mammalian genes are known e.g., from globin, elastase, albumin, α-fetoprotein and insulin genes. A suitable enhancer is an enhancer from a eukaryotic cell virus. Examples include the SV40 enhancer on the late side of the replication origin (bp 100-270), the enhancer of the cytomegalovirus immediate early promoter (Boshart et al. *Cell* 41:521 (1985)), the polyoma enhancer on the late side of the replication origin, and adenovirus enhancers (see also, e.g., Yaniv, *Nature,* 297:17-18 (1982) on enhancing elements for activation of eukaryotic promoters). The enhancer sequences may be introduced into the vector at a position 5' or 3' to the gene of interest, but is preferably located at a site 5' to the promoter.

Sometimes, the polynucleotide encoding the selectable gene and/or the polynucleotide of interest is preceded by DNA encoding a signal sequence having a specific cleavage site at the N-terminus of the mature protein or polypeptide. In general, the signal sequence may be a component designed into the basic expression vector, or it may be a part of the selectable gene or desired product gene that is inserted into the expression vector. If a heterologous signal sequence is used, it is preferably one that is recognized and processed (e.g., cleaved by a signal peptidase) by the host cell. For mammalian cell expression, the native signal sequence of the protein of interest may be used if the protein is of mammalian origin. Alternatively, the native signal sequence can be substituted by other suitable mammalian signal sequences, such as signal sequences from secreted polypeptides of the same or related species, as well as viral secretory leaders, for example, the herpes simplex gD signal. The DNA for such precursor region is operably linked in reading frame to the selectable gene or product gene.

The mammalian expression vectors will typically contain prokaryotic sequences that facilitate the propagation of the vector in bacteria. Therefore, the vector may have other components such as an origin of replication (e.g., a nucleic acid sequence that enables the vector to replicate in one or more selected host cells), antibiotic resistance genes for selection in bacteria, and/or an amber stop codon which can permit translation to read through the codon. Additional eukaryotic selectable gene(s) may be incorporated. Generally, in cloning vectors the origin of replication is one that enables the vector to replicate independently of the host chromosomal DNA, and includes origins of replication or autonomously replicating sequences. Such sequences are well known, e.g., the ColE1 origin of replication in bacteria. Various viral origins (e.g., SV40, polyoma, adenovirus, VSV or BPV) are useful for cloning vectors in mammalian cells. Generally, a eukaryotic replicon is not needed for expression in mammalian cells unless extrachromosomal (episomal) replication is intended (e.g., the SV40 origin may typically be used only because it contains the early promoter).

The present constructs, for example, constructs comprising triple tag sequences (e.g., SEQ ID NOs: 1, 2 and 3 or SEQ ID NO: 4 or SEQ ID NO: 5) can accommodate a wide variety of nucleotide sequence inserts. To facilitate insertion and expression of different genes of interest (e.g., coding for proteins of interest) from the constructs and expression vectors of the disclosure, the constructs are designed with at least one cloning site for insertion of any gene of interest (e.g., coding for any protein of interest including an antibody such as a single chain antibody or a Fab). Preferably, the cloning site is a multiple cloning site, e.g., containing multiple restriction sites.

The plasmids can be propagated in bacterial host cells to prepare DNA stocks for subcloning steps or for introduction into eukaryotic host cells. Transfection of eukaryotic host cells can be any performed by any method well known in the art. Transfection methods include lipofection, electroporation, calcium phosphate co-precipitation, rubidium chloride or polycation mediated transfection, protoplast fusion and microinjection. Preferably, the transfection is a stable transfection. The transfection method that provides optimal transfection frequency and expression of the construct in the particular host cell line and type, is favored. Suitable methods can be determined by routine procedures. For stable transfectants, the constructs are integrated so as to be stably maintained within the host chromosome.

Host cells suitable for expression of the selected sequence and the amplifiable selectable marker include eukaryotic cells, preferably mammalian cells. The cell type should be capable of expressing the construct encoding the desired protein, processing the protein and transporting a secreted protein to the cell surface for secretion. Processing includes co- and post-translational modification such as leader peptide cleavage, GPI attachment, glycosylation, ubiquitination, and disulfide bond formation. Immortalized host cell cultures amenable to transfection and in vitro cell culture and of the kind typically employed in genetic engineering are preferred. Examples of useful mammalian host cell lines are monkey kidney CV1 line transformed by SV40 (COS-7, ATCC CRL 1651); human embryonic kidney line (293 or 293 derivatives adapted for growth in suspension culture, Graham et al., *J. Gen Virol.,* 36:59 (1977); baby hamster kidney cells (BHK, ATCC CCL 10); DHFR⁻Chinese hamster ovary cells (ATCC CRL-9096); dp12.CHO cells, a derivative of CHO/DHFR- (EP 307,247 published 15 Mar. 1989); mouse sertoli cells (TM4, Mather, *Biol. Reprod.,* 23:243-251 (1980)); monkey kidney cells (CV1 ATCC CCL 70); African green monkey kidney cells (VERO-76, ATCC CRL-1587); human cervical carcinoma cells (HELA, ATCC CCL 2); canine kidney cells (MDCK, ATCC CCL 34); buffalo rat liver cells (BRL 3A, ATCC CRL 1442); human lung cells (W138, ATCC CCL 75); human liver cells (Hep G2, HB 8065); mouse mammary tumor (MMT 060562, ATCC CCL51); TR1 cells (Mather et al., *Annals N.Y. Acad. Sci.,* 383:44-68 (1982)); PEER human acute lymphoblastic cell line (Ravid et al. *Int. J. Cancer* 25:705-710 (1980)); MRC 5 cells; FS4 cells; human hepatoma line (Hep G2), human HT1080 cells, KB cells, JW-2 cells, Detroit 6 cells, NIH-3T3 cells, hybridoma and myeloma cells. Embryonic cells used for generating transgenic animals are also suitable (e.g., zygotes and embryonic stem cells).

Signal Peptide Component

A signal peptide (e.g., a signal sequence) may be fused in frame to the N-terminus of a protein of interest (e.g. an antibody such as a single chain antibody, a single domain antibody or a Fab or a peptide, such as a non-antibody peptide). The signal peptide may be a protein sequence that directs proteins to which it is fused to the periplasmic space of bacteria. In some embodiments, the signal peptide may be derived from a bacteriophage protein. Signal peptides useful in the present disclosure include, for example, the N-terminal signal peptide from the bacteriophage proteins pIII, pVIII, pVII, and pIX. The bacteriophage proteins can be from bacteriophages such as, filamentous bacteriophage, lambda, T4 or MS2. In a preferred embodiment the signal peptide may be derived from filamentous bacteriophage, such as M13, Fd, Fl, or Ke.

The DNA sequences encoding the signal peptides may be obtained from natural sources, for example amplified by PCR from bacteriophage genomic DNA, or can be made synthetically using synthetic oligonucleotides. Signal sequences useful in the present disclosure are disclosed in WO 03/004636.

Partial signal sequences and variants may also be used as long as the encoded signal peptide sequence directs the polypeptide sequence to which it is attached to the periplasm of bacteria. In some embodiments, hybrid signal peptides that comprise amino acid sequences from at least 2 different signal peptides may be used.

Signal sequences may include, for example, a prokaryotic signal sequence, such as a pectate lyase signal sequence (pelB) (MKYLLPTAAAGLLLLAAQPAMA (SEQ ID NO: 7) (see, e.g., U.S. Pat. Nos. 5,576,195 and 5,846,818). Eukaryotic signal sequences for prokaryotic expression may include, for example, MKILILGIFLFLCSTPAWA (SEQ ID NO: 8), MRTLAILAAILLVALQAQA (SEQ ID NO: 9), and MGALAVFAVACLAAVASVAHA (SEQ ID NO: 10) (see, e.g., U.S. Pat. Nos. 7,094,579 and 7,396,661).

Protein of Interest Component

The triple tag sequence of the present disclosure may be linked to a protein of interest. The protein of interest may be any protein known in the art. In some embodiments, the protein of interest may be an antibody, for example, a single chain antibody (e.g., scFv), a single domain antibody or Fab fragment. In some embodiments, the single chain antibody comprises a $V_H$ linked by a linker to a $V_L$ (e.g., $V_H$-L-$V_L$ or $V_L$-L-$V_H$). In some embodiments, the protein of interest is a peptide.

An immunoglobulin variable region includes: i) an antibody heavy chain variable domain ($V_H$), or antigen binding fragment thereof, with or without constant region domains ii) an antibody light chain variable domain ($V_L$), or antigen binding fragment thereof, with or without constant region domains iii) a $V_H$ or $V_L$ domain polypeptide without constant region domains linked to another variable domain (a $V_H$ or $V_L$ domain polypeptide) that is with or without constant region domains, (e.g., $V_H$-$V_H$, $V_H$-$V_L$, or $V_L$-$V_L$), and iv) single-chain Fv antibodies (scFv), that is a $V_L$ domain polypeptide without constant regions linked to another $V_H$ domain polypeptide without constant regions ($V_H$-$V_L$ or $V_L$-$V_H$), the variable domains together forming an antigen binding site, including, for example, wherein $V_H$ is linked by a linker to $V_L$ (e.g., $V_H$-L-$V_L$ or $V_L$-L-$V_H$). In an embodiment of option (i), (ii), or (iii), each variable domain forms and antigen binding site independently of any other variable domain. Option (i) or (ii) can be used to form a Fab fragment antibody or an Fv antibody. Thus, an immunoglobulin variable region polypeptide includes antibodies that may or may not contain constant region domains. In addition, immunoglobulin variable region polypeptides include antigen binding antibody fragments that can contain either all or just a portion of the corresponding heavy or light chain constant regions. In addition, an immunoglobulin variable region polypeptide include light chain, heavy chain, heavy and light chains (e.g., scFv), Fd (e.g., $V_H$-$C_{H1}$) or $V_L$-$C_L$. In addition, the term immunoglobulin variable region polypeptide can contain either all or just a portion of the corresponding heavy or light chain constant regions.

Single-domain antibodies (e.g., dAb) may include: i) an antibody comprising heavy chain variable domain ($V_H$), or antigen binding fragment thereof, which forms an antigen binding site independently of any other variable domain, ii) an antibody comprising a light chain variable domain ($V_L$), or antigen binding fragment thereof, which forms an antigen binding site independently of any other variable domain, iii) an antibody comprising a $V_H$ domain polypeptide linked to another $V_H$ or a $V_L$ domain polypeptide (e.g., $V_H$-$V_H$ or $V_H$-$V_L$), wherein each V domain forms an antigen binding site independently of any other variable domain, and iv) an antibody comprising $V_L$ domain polypeptide linked to another $V_L$ domain polypeptide ($V_L$-$V_L$), wherein each V domain forms an antigen binding site independently of any other variable domain. The $V_L$ domain may refer to both the kappa and lambda forms of the light chains.

In some embodiments the protein of interest may be a protein scaffold. Libraries of protein scaffolds capable of specifically binding to antigens are available in the art. These include: Adnectins, Affibodies, Anticalins, DARPins, engineered Kunitz-type inhibitors, tetranectins, A-domain proteins, lipocalins, repeat proteins such as ankyrin repeat proteins, immunity proteins, α2p8 peptide, insect defensin A, PDZ domains, charybdotoxins, PHD fingers, TEM-1, β-lactamase, fibronectin type III domains, CTLA-4, T-cell resptors, knottins, neocarzinostatin, carbohydrate binding module 4-2, green fluorescent protein, thioredoxin (Gebauer & Skerra, Curr. Opin. Chem. Biol. 13:245-55 (2009); Gill & Damle, Curr. Opin. Biotech 17: 653-58 (2006); Hosse et al, Protein Sci. 15:14-27 (2006); Skerra, Curr. Opin. Biotech 18: 295-3-4 (2007)).

A linker may include peptide linkers, as well as to chemical bond linkages, such as linkages by disulfide bonds or by chemical bridges.

Methods for preparing fragments of genomic DNA where immunoglobulin variable regions can be cloned as a diverse population are well known in the art (see, e.g., Hermann et al., Methods in Enzymology, 152: 180-183, (1987); Frischauf, Methods in Enzymology, 152:183-190 (1987); Frischauf, Methods in Enzymology, 152:190-199 (1987); and DiLella et al., Methods in Enzymology, 152: 199-212 (1987)).

For example, DNA encoding a monoclonal antibody may be isolated and sequenced from a hybridoma cell secreting the antibody using conventional procedures (e.g., by using oligonucleotide probes that are capable of binding specifically to genes encoding the heavy and light chains of the monoclonal antibodies). Sequence determination will generally require isolation of at least a portion of the gene or cDNA of interest. Usually this requires cloning the DNA or, preferably, mRNA (e.g., cDNA) encoding the monoclonal antibodies. Cloning is carried out using standard techniques (see, e.g., Sambrook et al. (1989) Molecular Cloning: A Laboratory Manual, Vols 1-3, Cold Spring Harbor Press). For example, a cDNA library may be constructed by reverse transcription of polyA+ mRNA, preferably membrane-associated mRNA, and the library screened using probes specific for human immunoglobulin polypeptide gene sequences. Nucleotide probe reactions and other nucleotide hybridization reactions are carried out at conditions enabling the identification of polynucleotides which hybridize to each other under specified conditions.

One exemplary set of conditions is as follows: stringent hybridization at 42° C. in 50% formamide, 5×SSC, 20 mM Na.PO4, pH 6.8; and washing in 1×SSC at 55° C. for 30 minutes. Formula for calculating equivalent hybridization conditions and/or selecting other conditions to achieve a desired level of stringency are well known. It is understood in the art that conditions of equivalent stringency can be achieved through variation of temperature and buffer, or salt concentration as described in Ausubel, et al. (Eds.), Protocols in Molecular Biology, John Wiley & Sons (1994), pp. 6.0.3 to 6.4.10. Modifications in hybridization conditions can be empirically determined or precisely calculated based on the length and the percentage of guanosine/cytosine (GC) base pairing of the probe. The hybridization conditions can be calculated as described in Sambrook, et al., (Eds.), Molecular Cloning: A Laboratory Manual, Cold Spring Harbor Laboratory Press: Cold Spring Harbor, N.Y. (1989), pp. 9.47 to 9.51

In some embodiments, the polymerase chain reaction (PCR) may be used to amplify cDNAs (or portions of full-length cDNAs) encoding an immunoglobulin gene segment of interest (e.g., a light chain variable segment). The amplified sequences can be readily cloned into any suitable vector, e.g., expression vectors, minigene vectors, or phage display vectors. It will be appreciated that the particular method of cloning used is not critical, so long as it is possible to determine the sequence of some portion of the immunoglobulin polypeptide of interest. An isolated nucleic acid molecule or isolated nucleic acid sequence is a nucleic acid molecule that may be either (1) identified and separated from at least one contaminant nucleic acid molecule with which it is ordinarily associated in the natural source of the nucleic acid or (2) cloned, amplified, tagged, or otherwise distinguished from background nucleic acids such that the sequence of the nucleic acid of interest can be determined, is considered isolated. An isolated nucleic acid molecule is other than in the form or setting in which it is found in nature. Isolated nucleic acid molecules therefore are distinguished from the nucleic acid molecule as it exists in natural cells. However, an isolated nucleic acid molecule includes a nucleic acid molecule contained in cells that ordinarily express the antibody where, for example, the nucleic acid molecule is in a chromosomal location different from that of natural cells.

One source for RNA used for cloning and sequencing is a hybridoma produced by obtaining a B cell from the transgenic mouse and fusing the B cell to an immortal cell. Alternatively, RNA can be isolated from B cells (or whole spleen) of the immunized animal. When sources other than hybridomas are used, it may be desirable to screen for sequences encoding immunoglobulins or immunoglobulin polypeptides with specific binding characteristics. One method for such screening is the use of phage display technology. Phage display is described further herein and is also well-known in the art (see, e.g., Dower et al., WO 91/17271; McCafferty et al., WO 92/01047; and Caton and Koprowski, *Proc. Natl. Acad. Sci. USA*, 87:6450-54 (1990)). In one embodiment, cDNA from an immunized transgenic mouse (e.g., total spleen cDNA) is isolated, the polymerase chain reaction is used to amplify a cDNA sequences that encode a portion of an immunoglobulin polypeptide, e.g., CDR regions, and the amplified sequences are inserted into a phage vector. cDNAs encoding peptides of interest, e.g., variable region peptides with desired binding characteristics, are identified by standard phage display techniques such as panning.

The sequence of the amplified or cloned nucleic acid is then determined. Typically the sequence encoding an entire variable region of the immunoglobulin polypeptide is determined, however, it will sometimes by adequate to sequence only a portion of a variable region, for example, the CDR-encoding portion. Typically the portion sequenced will be at least 30 bases in length, more often based coding for at least about one-third or at least about one-half of the length of the variable region will be sequenced.

Sequencing can be carried out on clones isolated from a cDNA library, or, when PCR is used, after subcloning the amplified sequence or by direct PCR sequencing of the amplified segment. Sequencing is carried out using standard techniques (see, e.g., Sambrook et al. (1989) Molecular Cloning: A Laboratory Guide, Vols 1-3, Cold Spring Harbor Press, and Sanger, F. et al. (1977) Proc. Natl. Acad. Sci. USA 74: 5463-5467). By comparing the sequence of the cloned nucleic acid with published sequences of human immunoglobulin genes and cDNAs, one of skill will readily be able to determine, depending on the region sequenced, (i) the germline segment usage of the hybridoma immunoglobulin polypeptide (including the isotype of the heavy chain) and (ii) the sequence of the heavy and light chain variable regions, including sequences resulting from N-region addition and the process of somatic mutation. One source of immunoglobulin gene sequence information is the National Center for Biotechnology Information, National Library of Medicine, National Institutes of Health, Bethesda, Md.

Bacteriophage Coat Protein Component

A variety of bacteriophage systems and bacteriophage coat proteins may be used to display proteins of interest (e.g., antibodies, including single chain antibodies, single domain antibodies or Fab fragments of antibodies or peptide including non-antibody peptides) linked to a triple tag sequence (e.g., a triple tag sequence comprising 6× histidine (SEQ ID NO: 1), c-myc (SEQ ID NO: 2) and V5 (SEQ ID NO: 3), or SEQ ID NO: 4, or SEQ ID NO: 5). Examples of suitable bacteriophage coat proteins include, without limitation, M13 gene III, gene VIII; rd minor coat protein pIII (Saggio et al., *Gene* 152:35, 1995); lambda D protein (Sternberg & Hoess, *Proc. Natl. Acad. Sci. USA* 92:1609, 1995; Mikawa et al., *J. Mol. Biol.* 262:21, 1996); lambda phage tail protein pV (Maruyama et al., *Proc. Natl. Acad. Sci. USA* 91:8273, 1994; U.S. Pat. No. 5,627,024); fr coat protein (WO96/11947; DD 292928; DD 286817; DD 300652); φ29 tail protein gp9 (Lee, *Virol.* 69:5018, 1995); MS2 coat protein; T4 small outer capsid protein (Ren et al., *Protein Sci.* 5:1833, 1996), T4 nonessential capsid scaffold protein IPIII (Hong and Black, *Virology* 194:481, 1993), or T4 lengthened fibritin protein gene (Efimov, *Virus Genes* 10:173, 1995); PRD-1 gene III; Q.beta.3 capsid protein (as long as dimerization is not interfered with); and P22 tailspike protein (Carbonell and Villayerde, *Gene* 176:225, 1996). Techniques for inserting foreign coding sequence into a phage gene are well known (see e.g., Sambrook et al., Molecular Cloning: A Laboratory Manual, Cold Spring Harbor Press, NY, 1989; Ausubel et al., Current Protocols in Molecular Biology, Greene Publishing Co., NY, 1995).

In an embodiment of the disclosure, a filamentous bacteriophage coat protein may be used. Many filamentous bacteriophage vectors are commercially available that can allow for the in-frame ligation of a polypeptide fusion protein comprising a signal peptide, one or more immunoglobulin variable regions and a triple tag sequence. The most common vectors accept DNA inserts for in frame fusions with gene III or gene VIII or truncated version of gene III or gene VIII. Truncated version of pIII may include the sequence represented by SEQ ID NO: 18. Non-limiting examples of suitable vectors include, M13 mp vectors (Pharmacia Biotech), pCANTAB 5e (Pharmacia Biotech), pCOMB3 and M13KE (New England Biolabs), pBluescript series (Stratagene Cloning Systems, La Jolla, Calif.). It should be understood that these vectors already contain bacteriophage signal peptide sequences and that each vector can be modified to contain an alternative signal peptide sequence of interest by methods well known in the art (see, e.g., Sambrook et al., Molecular Biology: A laboratory Approach, Cold Spring Harbor, N.Y. 1989; and Ausubel, et al., Current protocols in Molecular Biology, Greene Publishing, Y, 1995).

Construction of Vectors

The triple tag sequence of the present disclosure may be fused in frame with a protein of interest, which can be fused in frame to a bacteriophage protein (see, e.g., Example 1 and FIGS. 1-5). The vectors can be constructed using standard methods (see, e.g., Sambrook et al., Molecular Biology: A Laboratory Manual, Cold Spring Harbor, N.Y. 1989; and Ausubel, et al., Current Protocols in Molecular Biology, Greene Publishing, Co. N.Y, 1995), guided by the principles discussed below. In brief, conventional ligation techniques are used to insert DNA sequences encoding the protein of interest and triple tag sequence into an expression vector. The sequences are ligated such that the components are expressed as an in-frame fusion. In an embodiment, the DNA encoding the protein of interest is ligated in frame to a bacteriophage coat protein in order that protein of interest can be displayed on the surface of a bacteriophage particle.

Vectors and Host Cells

The manipulation of polynucleotides of the present disclosure including polynucleotides coding for a protein of interest and a triple tag sequence is typically carried out in recombinant vectors. Both phagemid and non-phagemid vectors can be used. Numerous vectors are publicly available, including bacterial plasmids, bacteriophage, artificial chromosomes, episomal vectors and gene expression vectors can be employed. A vector of use according to the disclosure may be selected to accommodate a polypeptide coding sequence of a desired size. A suitable host cell is transformed with the vector after in vitro cloning manipulations. Host cells may be prokaryotic, such as any of a number of bacterial strains, or may be eukaryotic, such as yeast or other fungal cells, insect or amphibian cells, or mammalian cells including, for example, rodent, simian or human cells. Each vector contains various functional components, which generally include a cloning site, an origin of replication and at least one selectable marker gene. If given vector is an expression vector, it additionally possesses one or more of the following: enhancer element, promoter, transcription termination and signal sequences, each positioned in the vicinity of the cloning site, such that they are operatively linked to the gene encoding a polypeptide repertoire member according to the disclosure.

Both cloning and expression vectors generally contain nucleic acid sequences that enable the vector to replicate in one or more selected host cells. Typically in cloning vectors, this sequence is one that enables the vector to replicate independently of the host chromosomal DNA and includes origins of replication or autonomously replicating sequences. Such sequences are well known for a variety of bacteria, yeast and viruses. For example, the origin of replication from the plasmid pBR322 is suitable for most Gram-negative bacteria, the 2 micron plasmid origin is suitable for yeast, and various viral origins (e:g. SV 40, adenovirus) are useful for cloning vectors in mammalian cells. Generally, the origin of replication is not needed for mammalian expression vectors unless these are used in mammalian cells able to replicate high levels of DNA, such as COS cells.

A cloning or expression vector may contain a selection gene also referred to as a selectable marker. This gene encodes a protein necessary for the survival or growth of transformed host cells grown in a selective culture medium. Host cells not transformed with the vector containing the selection gene will therefore not survive in the culture medium. Typical selection genes encode proteins that confer resistance to antibiotics and other toxins, e.g. ampicillin, neomycin, methotrexate or tetracycline, complement auxotrophic deficiencies, or supply critical nutrients not available in the growth media.

Since the replication of vectors according to the present disclosure is most conveniently performed in E. coli (e.g., strain TB1 or TG1), an E. coli-selectable marker, for example, the β-lactamase gene that confers resistance to the antibiotic ampicillin, is of use. These can be obtained from E. Coli plasmids, such as pBR322 or a pUC plasmid such as pUC18 or pUC19, or pUC119.

Expression vectors usually contain a promoter that is recognized by the host organism and is operably linked to the coding sequence of interest. Such a promoter may be inducible or constitutive. Polynucleotides are operably linked when the polynucleotides are in a relationship permitting them to function in their intended manner.

Promoters suitable for use with prokaryotic hosts include, for example, the α-lactamase and lactose promoter systems, alkaline phosphatase, the tryptophan (trp) promoter system and hybrid promoters such as the tac promoter. Promoters for use in bacterial systems will also generally contain a Shine-Delgamo sequence operably linked to the coding sequence.

In a preferred aspect of the disclosure a filamentous bacteriophage vector system is used for expression of a polypeptide fusion protein comprising a signal peptide, one or more immunoglobulin variable regions and a triple tag sequence in order that the fusion proteins can be incorporated into bacteriophage for display on the outer surface of the bacteriophage particle. Many filamentous bacteriophage vectors (phage vectors) are commercially available for use that allow for the in-frame ligation of the DNA encoding the immunoglobulin variable region polypeptide fusion protein to a bacteriophage coat protein. The most common vectors accept DNA inserts for in frame fusions with gene III or gene VIII. Non-limiting examples of suitable vectors include, M13 mp vectors (Pharmacia Biotech), pCANTAB 5e (Pharmacia Biotech), pCOMB3 and M13KE (New England Biolabs), and others as described in WO 00/29555. It should be understood that these vectors already contain bacteriophage signal peptide sequences and that each vector can be modified to contain an alternative signal peptide sequence of interest by methods well known in the art (see, e.g., Sambrook et al., Molecular Biology: A Laboratory Manual, Cold Spring Harbor, N.Y. 1989; and Ausubel, et al., Current protocols in Molecular Biology, Greene Publishing, Co. N.Y, 1995).

Introduction of Vectors to Host Cells.

Vectors (e.g., phagemid or phage vectors) useful in the present disclosure may be introduced to selected host cells by any of a number of suitable methods known to those skilled in the art. For example, vector constructs may be introduced to appropriate bacterial cells by infection, in the case of E. coli bacteriophage vector particles such as lambda or M13, or by any of a number of transformation methods for plasmid vectors or for bacteriophage DNA. For example, standard calcium-chloride-mediated bacterial transformation is still commonly used to introduce naked DNA to bacteria (see, e.g., Sambrook et al., 1989, Molecular Cloning, A Laboratory Manual, Cold Spring Harbor Laboratory Press, Cold Spring Harbor, N.Y.), but electroporation may also be used (see, e.g., Ausubel et al., 1988, Current Protocols in Molecular Biology, John Wiley & Sons, Inc., NY, N.Y.).

For the introduction of vector constructs to yeast or other fungal cells, chemical transformation methods are generally used (e.g., Rose et al., 1990, Methods in Yeast Genetics, Cold Spring Harbor Laboratory Press, Cold Spring Harbor, N.Y.). For transformation of S. cerevisiae, for example, the cells are treated with lithium acetate to achieve transformation efficiencies of approximately 104 colony-forming units (transformed cells)/μg of DNA. Transformed cells are then isolated on selective media appropriate to the selectable marker used. Alternatively, or in addition, plates or filters lifted from plates may be scanned for GFP fluorescence to identify transformed clones.

For the introduction of vectors comprising differentially expressed sequences to mammalian cells, the method used will depend upon the form of the vector. Plasmid vectors may be introduced by any of a number of transfection methods, including, for example, lipid-mediated transfection ("lipofection"), DEAE-dextran-mediated transfection, electroporation or calcium phosphate precipitation (see, e.g., Ausubel et al., 1988, Current Protocols in Molecular Biology, John Wiley & Sons, Inc., NY, N.Y.).

Lipofection reagents and methods suitable for transient transfection of a wide variety of transformed and non-transformed or primary cells are widely available, making lipofection an attractive method of introducing constructs to eukaryotic, and particularly mammalian cells in culture. For example, LipofectAMINE™ (Life Technologies) or Lipo-Taxi™ (Stratagene) kits are available. Other companies offering reagents and methods for lipofection include Bio-Rad Laboratories, CLONTECH, Glen Research, InVitrogen, JBL Scientific, MBI Fermentas, PanVera, Promega, Quantum Biotechnologies, Sigma-Aldrich, and Wako Chemicals USA.

Suitable host cells for cloning or expressing the polynucleotides (e.g., DNA) in the vectors herein are prokaryote, yeast, or higher eukaryote cells. Polynucleotides or vectors include polynucleotides coding for a protein of interest and a triple tag sequence. Suitable prokaryotes for this purpose include eubacteria, such as Gram-negative or Gram-positive organisms, for example, Enterobacteriaceae such as *Escherichia*, e.g., *E. coli, Enterobacter, Erwinia, Klebsiella, Proteus, Salmonella*, e.g., *Salmonella typhimurium, Serratia*, e.g., *Serratia marcescans*, and *Shigella*, as well as Bacilli such as *B. subtilis* and *B. licheniformis* (e.g., *B. licheniformis* 41 P disclosed in DD 266,710 published Apr. 12, 1989), *Pseudomonas* such as *P. aeruginosa*, and *Streptomyces*. One preferred *E. coli* cloning host is *E. coli* 294 (ATCC 31,446), although other strains such as *E. coli* B, *E. coli* X1776 (ATCC 31,537), and *E. coli* W3110 (ATCC 27,325) are suitable.

In addition to prokaryotes, eukaryotic microbes such as filamentous fungi or yeast are suitable cloning or expression hosts for vectors comprising polynucleotides coding for proteins of interest including antibodies (e.g., antibody-encoding vectors). *Saccharomyces cerevisiae*, or common baker's yeast, is the most commonly used among lower eukaryotic host microorganisms. However, a number of other genera, species, and strains are commonly available and useful herein, such as *Schizosaccharomyces pombe; Kluyveromyces* hosts such as, e.g., *K. lactis, K. fragilis* (ATCC 12,424), *K. bulgaricus* (ATCC 16,045), *K. wickeramii* (ATCC 24,178), *K. waltii* (ATCC 56,500), *K. drosophilarum* (ATCC 36,906), *K. thermotolerans*, and *K. marxianus; yarrowia* (EP 402,226); *Pichia* pastors (EP 183,070); *Candida; Trichoderma reesia* (EP 244,234); *Neurospora crassa; Schwanniomyces* such as *Schwanniomyces occidentalis*; and filamentous fungi such as, e.g., *Neurospora, Penicillium, Tolypocladium*, and *Aspergillus* hosts such as *A. nidulans* and *A. niger*.

Suitable host cells for the expression of glycosylated antibody are derived from multicellular organisms. Examples of invertebrate cells include plant and insect cells. Numerous baculoviral strains and variants and corresponding permissive insect host cells from hosts such as *Spodoptera frugiperda* (caterpillar), *Aedes aegypti* (mosquito), *Aedes albopictus* (mosquito), *Drosophila melanogaster* (fruiffly), and *Bombyx mori* have been identified. A variety of viral strains for transfection are publicly available, e.g., the L-1 variant of *Autographa californica* NPV and the Bm-5 strain of *Bombyx mori* NPV, and such viruses may be used as the virus herein according to the present invention, particularly for transfection of *Spodoptera frugiperda* cells.

Plant cell cultures of cotton, corn, potato, soybean, petunia, tomato, tobacco, lemna, and other plant cells can also be utilized as hosts.

Examples of useful mammalian host cell lines are Chinese hamster ovary cells, including CHOK1 cells (ATCC CCL61), DXB-11, DG-44, and Chinese hamster ovary cells/−DHFR (CHO, Urlaub et al., *Proc. Natl. Acad. Sci. USA* 77: 4216 (1980)); monkey kidney CV1 line transformed by SV40 (COS-7, ATCC CRL 1651); human embryonic kidney line (293 or 293 cells subcloned for growth in suspension culture, (Graham et al., *J. Gen Virol.* 36: 59, 1977); baby hamster kidney cells (BHK, ATCC CCL 10); mouse sertoli cells (TM4, Mather, (*Biol. Reprod.* 23: 243-251, 1980); monkey kidney cells (CV1 ATCC CCL 70); African green monkey kidney cells (VERO-76, ATCC CRL-1587); human cervical carcinoma cells (HELA, ATCC CCL 2); canine kidney cells (MDCK, ATCC CCL 34); buffalo rat liver cells (BRL 3A, ATCC CRL 1442); human lung cells (W138, ATCC CCL 75); human liver cells (Hep G2, HB 8065); mouse mammary tumor (MMT 060562, ATCC CCL51); TR1 cells (Mather et al., *Annals N.Y. Acad. Sci.* 383: 44-68 (1982)); MRC 5 cells; FS4 cells; and a human hepatoma line (Hep G2).

Host cells are transformed or transfected with the above-described expression or cloning vectors for production of proteins of interest, for example, antibody production or with polynucleotides coding for proteins of interest, for example, antibodies and cultured in conventional nutrient media modified as appropriate for inducing promoters, selecting transformants, or amplifying the genes encoding the desired sequences. In addition, novel vectors and transfected cell lines with multiple copies of transcription units separated by a selective marker are particularly useful and preferred for the expression of antibodies that bind the desired antigen.

Host cells containing desired nucleic acid sequences coding for proteins of interest including, for example, antibodies may be cultured in a variety of media. Commercially available media such as Ham's F10 (Sigma), Minimal Essential Medium ((MEM), Sigma), RPMI-1640 (Sigma), and Dulbecco's Modified Eagle's Medium ((DMEM), Sigma) are suitable for culturing the host cells. In addition, any of the media described in Ham et al., *Meth. Enz.* 58: 44, (1979); Barnes et al., *Anal. Biochem.* 102: 255 (1980); U.S. Pat. Nos. 4,767,704; 4,657,866; 4,927,762; 4,560,655; or U.S. Pat. No. 5,122,469; WO90103430; WO 87/00195; or U.S. Pat. Re. No. 30,985 may be used as culture media for the host cells. Any of these media may be supplemented as necessary with hormones and/or other growth factors (such as insulin, transferrin, or epidermal growth factor), salts (such as sodium chloride, calcium, magnesium, and phosphate), buffers (such as HEPES), nucleotides (such as adenosine and thymidine), antibiotics (such as GENTAMYCIN™ drug), trace elements (defined as inorganic compounds usually present at final concentrations in the micromolar range), and glucose or an equivalent energy source. Any other necessary supplements may also be included at appropriate concentrations that would be known to those skilled in the art. The culture conditions, such as temperature, pH, and the like, are those previously used with the host cell selected for expression, and will be apparent to the ordinarily skilled artisan.

When using recombinant techniques, the protein of interest including, for example, an antibody (e.g., a single chain antibody, a single domain antibody or a Fab) can be produced intracellularly, in the periplasmic space, or directly secreted into the medium, including from microbial cultures. If the antibody is produced intracellularly, as a first step, the particulate debris, either host cells or lysed fragments, is removed, for example, by centrifugation or ultrafiltration. Better et al. (*Science* 240:1041-43, 1988; ICSU Short Reports 10:105 (1990); and *Proc. Natl. Acad. Sci. USA* 90:457-461 (1993) describe a procedure for isolating antibodies which are secreted to the periplasmic space of *E. coli* (see also, e.g., Carter et al., *Bio/Technology* 10:163-167 (1992)). Periplasmic extracts can be prepared using methods known to those skilled in the art (see, e.g., Raffa R. L., *Periplasmic Expression and Purification of Recombinant Fabs*, from *Methods in Molecular Biology: Antibody Phage Display: Methods and Protocols* (2002) 178: 343-348 (O'Brien and Aitken, eds., Human Press, Totowa, N.J.); Barbas et al *Phage Display: A Laboratory Manual*, Cold Spring Harbor Laboratory Press, New York (2001).

The antibody composition prepared from microbial or mammalian cells can be purified using, for example, hydroxylapatite chromatography cation or avian exchange chromatography, and affinity chromatography, with affinity chromatography being the preferred purification technique. The suitability of protein A as an affinity ligand depends on the species and isotype of any immunoglobulin Fc domain that is present in the antibody. Protein A can be used to purify antibodies that are based on human γ1, γ2, or γ4 heavy chains (see, e.g., Lindmark et al., *J. Immunol. Meth.* 62: 1-13, 1983). Protein G is recommended for all mouse isotypes and for human γ3 (see, e.g., Guss et al., *EMBO J.* 5:15671575 (1986)). The matrix to which the affinity ligand is attached is most often agarose, but other matrices are available. Mechanically stable matrices such as controlled pore glass or poly(styrenedivinyl)benzene allow for faster flow rates and shorter processing times than can be achieved with agarose. Where the antibody comprises a $C_H3$ domain, the Bakerbond ABX™resin (J. T. Baker, Phillipsburg, N.J.) is useful for purification. Other techniques for protein purification such as fractionation on an ion-exchange column, ethanol precipitation, Reverse Phase HPLC, chromatography on silica, chromatography on heparin SEPHAROSE™ chromatography on an anion or cation exchange resin (such as a polyaspartic acid column), chromatofocusing, SDS-PAGE, and ammonium sulfate precipitation are also available depending on the antibody to be recovered.

Construction of Libraries

Libraries of polynucleotides operably linked to a triple tag sequence of the present disclosure are provided including, for example, polynucleotides coding for a protein of interest linked to a polynucleotide coding for a triple tag sequence, wherein the triple tag sequence comprises 6× histidine (HHHHHH SEQ ID NO: 1), c-myc (EQKLISEEDL SEQ ID NO: 2) and V5 (GKPIPNPLLGLDST SEQ ID NO: 3), including wherein a c-myc tag is positioned between a 6× histidine tag and a V5 tag. In some embodiments, the 6× histidine (SEQ ID NO: 1), c-myc (SEQ ID NO: 2) and V5 (SEQ ID NO: 3) are directly linked. In some embodiments, the 6× histidine (SEQ ID NO: 1), c-myc (SEQ ID NO: 2) and V5 (SEQ ID NO: 3) are indirectly linked through one or more spacers. In some embodiments, the spacer is 3 to 7 amino acids in length. In some embodiments, the spacer is GAA or KAA. In some embodiments, the polynucleotide codes for a triple tag sequence that is represented by HHHHHHEQKLISEEDLGKPIPNPLLGLDST (SEQ ID NO: 4). In some embodiments, the polynucleotide codes for a triple tag sequence that is represented by HHHHHHGAAEQKLISEEDLKAAGKPIPNPLLGLDST (SEQ ID NO: 5). In some embodiments, the protein of interest is an antibody, for example, a single chain antibody, single domain antibody or Fab. In some embodiments, the protein of interest is a peptide, for example, a non-antibody peptide. The library can take the form of a simple mixture of polypeptides or nucleic acids, or can be in the form organisms or cells, for example bacteria, viruses, animal or plant cells and the like, transformed with a library of nucleic acids. Typically, each individual organism or cell contains only one member of the library. In certain applications, each individual organism or cell can contain two or more members of the library. The nucleic acids may be incorporated into expression vectors, in order to allow expression of the polypeptides encoded by the nucleic acids. In a preferred aspect, therefore, a library can take the form of a population of host organisms, each organism containing one or more copies of an expression vector containing a single member of the library in nucleic acid form which can be expressed to produce its corresponding polypeptide member. Thus, the population of host organisms has the potential to encode a large repertoire of genetically diverse polypeptide variants.

A number of vector systems useful for library production and selection are known in the art. For example, bacteriophage lambda expression systems can be screened directly as bacteriophage plaques or as colonies of lysogens, both as previously described (see, e.g., Huse et al., *Science*, 246: 1275-1281, 1989; Caton & Koprowski, Proc. Natl. Acad. Sci. USA, 87:6450-6454, 1990; Mullinax et al., Proc. Natl. Acad. Sci. USA, 87:8095-8099, 1990; and Persson et al., Proc. Natl. Acad. Sci. USA, 88:2432-2436, 1991) and are of use in the disclosure. While such expression systems can be used for screening up to $10^6$ different members of a library, they are not really suited to screening of larger numbers (greater than $10^6$ members). Other screening systems rely, for example, on direct chemical synthesis of library members. One early method involves the synthesis of peptides on a set of pins or rods, such as described in WO 84/03564. A similar method involving peptide synthesis on beads, which forms a peptide library in which each bead is an individual library member, is described in U.S. Pat. No. 4,631,211 and a related method is described in WO 92/00091.

Another chemical synthesis method involves the synthesis of arrays of peptides on a surface in a manner that places each distinct library member (e.g., unique peptide sequence) at a discrete, predefined location in the array, or the spotting of pre-formed polypeptides on such an array. The identity of each library member is determined by its spatial location in the array. The locations in the array where binding interactions between a predetermined molecule (e.g., a receptor) and reactive library members occur is determined, thereby identifying the sequences of the reactive library members on the basis of spatial location (see, e.g., U.S. Pat. No. 5,143,854; WO 90/15070 and WO 92/10092; Fodor et al., *Science*, 251: 767-773, 1991; and Dower & Fodor, Ann. Rep. Med. Chem., 26:271-280, 1991).

Any selection display system can be used in conjunction with a library according to the disclosure. Methods for display of polypeptides on the surface of viruses, yeast, microbial and mammalian cells are well known in the art (see, e.g., U.S. Pat. Nos. 5,348,867; 5,723,287; 6,699,658; Wittrup, Cum Op. Biotech. 12:395-99 (2001); Lee et al, Trends in Biotech. 21(1) 45-52 (2003); and Surgeeva et al., Adv. Drug Deliv. Rev. 58: 1622-54 (2006)). Polypeptide libraries may be attached to yeast proteins, such as agglutinin, effectively mimicking the cell surface display of antibodies by B cells in the immune system.

In addition to phage display methods, antibodies may be isolated using in vitro display methods including ribosome display and mRNA display (see, e.g., Amstutz et al., Curr. Op. Biotech. 12: 400-05 (2001)). Selection of polypeptide using ribosome display is described in Hanes et al., (Proc. Natl. Acad Sci USA, 94:4937-4942 (1997)) and U.S. Pat. Nos. 5,643,768 and 5,658,754 issued to Kawasaki. Ribosome display is also useful for rapid large scale mutational analysis of antibodies. The selective mutagenesis approach also provides a method of producing antibodies with improved activities that can be selected using ribosomal display techniques.

For example, immunoglobulin variable region polypeptide fusion proteins of the present disclosure may be displayed on lambda phage capsids (phage bodies). Preferred selection systems of the disclosure are the filamentous bacteriophage systems. Selection protocols for isolating desired members of large libraries are known in the art, as typified by phage display techniques. An advantage of phage-based display systems is that, because they are biological systems, selected library members can be amplified simply by growing the phage containing the selected library member in bacterial cells.

Methods for the construction of bacteriophage antibody display libraries and lambda phage expression libraries are well known in the art (see, e.g., McCafferty et al., Nature, 348:552-554, 1990; Kang et al., Proc. Natl. Acad. Sci. USA, 88:11120-11123, 1991; Clackson et al., Nature, 352:624-628, 1991; Lowman et al., Biochemistry, 30:10832-10838, 1991; Burton et al., Proc. Natl. Acad. Sci. USA, 88:10134-10137, 1991; Hoogenboom et al., Nucleic Acid Res., 19:4133-4137, 1991; Chang et al., J. Immunol., 147:3610-3614, 1991; Breitling et al., Gene, 104:147-153, 1991; Marks et al., J. Biol. Chem., 267:16007-16010, 1991; Barbas et al., Proc. Natl. Acad. Sci. USA, 89:10164-10168, 1992; Hawkins & Winter, Eur. J. Immunol., 22:867-870, 1992; Marks et al., J. Biol. Chem., 267:16007-16010, 1992; and Lerner et al., Science, 258:1313-1314, 1992). In brief, the nucleic acids encoding the immunoglobulin variable region polypeptide fusion proteins are cloned into a phage vector that comprises a bacteriophage packaging signal and a gene encoding at least one bacteriophage coat protein which allows for the incorporation of the nucleic acid into a phage particle.

Binding Molecules to Tag Sequences

Binding molecules including, for example, antibodies or binding fragments thereof, that bind to a tag sequence including 6× histidine (SEQ ID NO: 1), c-myc (SEQ ID NO: 2) or V5 (SEQ ID NO: 3), as described herein, are contemplated by the present disclosure.

Antibodies or binding fragments thereof specific for the triple tag sequence or components of the triple tag sequence may include, for example, commercially available antibodies or antibody fragments or may include those antibodies or antibody fragments produced by recombinant based methods. Such antibodies or binding fragments thereof may include, for example, polyclonal antibodies, monoclonal antibodies (mAbs), recombinant antibodies, chimeric antibodies, CDR-grafted antibodies, fully human antibodies, single chain antibodies, and/or bispecific antibodies, as well as fragments, including variants and derivatives thereof, provided by known techniques, including, but not limited to enzymatic cleavage, peptide synthesis or recombinant techniques.

Exemplary commercial antibodies to V5 include, but are not limited to, mouse monoclonal anti-V5 antibody (Invitrogen, catalog number R960-25); anti-V5 antibody (Invitrogen, catalog number 460705); mouse anti-V5 antibody (Zymed, catalog number 37-7500); mouse anti-V5 antibody (Accurate Chemical, catalog number MCA1360GA); mouse anti-V5 antibody, clone V5.J9 (Abcam, catalog number ab60188-100); mouse anti-6× his tag antibody, clone 3H2201 (Abcam, catalog number ab15145-50); rabbit polyclonal anti-V5 antibody (Abcam, catalog number ab9116-100); rabbit anti-V5 antibody (Chemicon, catalog number AB3792); and chicken anti-V5 antibody (Abcam, catalog number ab9113-100). A preferred anti-V5 antibody, suitable for use in capture methods, is mouse monoclonal anti-V5 antibody (Invitrogen, catalog number R960-25).

Exemplary commercial antibodies to c-myc include, but are not limited to, anti-c-myc mouse monoclonal antibody (9E10) (Roche, catalog number 11667149001); and mouse monoclonal anti-c-myc antibody (Zymed, catalog number 13-2500).

Exemplary commercial antibodies to 6× histidine include, but are not limited to, mouse monoclonal anti-penta-his antibody (Quiagen, catalog number 34660); and mouse anti-6× his antibody, clone AD1.1.10 (R&D Systems, catalog number MAB050). A preferred anti-6×his antibody, suitable for use in capture methods, is mouse anti-6×his antibody, clone AD1.1.10 (R&D Systems, catalog number MAB050).

Antibodies or binding fragments thereof may be tailored to have a binding affinity for the triple tag sequence or a component of the triple tag sequence that is suited for its particular use (e.g., capture or detection). Antibodies or binding fragments thereof for capture of the triple tag sequence or a component of the triple tag sequence may have a $k_{off}$ of about $10^{-4}$, preferably about $10^{-5}$ or about $10^{-6}$ or less (e.g., slower off rate). Antibodies or binding fragments thereof for detection of the triple tag sequence or a component of the triple tag sequence may have a $k_{off}$ of about $10^{-2}$, preferably about $10^{-3}$ or less (e.g., slower off rate).

Polyclonal antibodies are preferably raised in animals by multiple subcutaneous (sc) or intraperitoneal (ip) injections of the relevant tag and an adjuvant. An improved antibody response may be obtained by conjugating the relevant tag sequence to a protein that is immunogenic in the species to be immunized, e.g., keyhole limpet hemocyanin, serum albumin, bovine thyroglobulin, or soybean trypsin inhibitor using a bifunctional or derivatizing agent, for example, maleimidobenzoyl sulfosuccinimide ester (conjugation through cysteine residues), N-hydroxysuccinimide (through lysine residues), glutaraldehyde, succinic anhydride or other agents known in the art.

Animals (e.g., rabbits or mice) may be immunized against the tag, immunogenic conjugates, or derivatives by combining the tag immunogenic conjugate or derivative with Freund's complete adjuvant and injecting the solution intradermally at multiple sites. Subsequently, for example, one month later, the animals are boosted with an amount of tag, protein or conjugate (e.g., less than the original amount) in Freund's complete adjuvant by subcutaneous injection at multiple sites. Subsequently, for example, at 7-14 days post-booster injection, the animals are bled and the serum is assayed for antibody titer. Animals are boosted until the titer plateaus. Preferably, the animal is boosted with the conjugate of the same tag, but conjugated to a different protein and/or through a different cross-linking reagent. Conjugates also can be made in recombinant cell culture as protein fusions. Also, aggregating agents such as alum are suitably used to enhance the immune response.

Monoclonal antibodies to be used in accordance with the present invention may be made by the hybridoma method first described by Kohler et al., (Nature, 256:495-7, 1975), or may be made by recombinant DNA methods (see, e.g., U.S. Pat. No. 4,816,567). The monoclonal antibodies may also be isolated from phage antibody libraries using the techniques described in, for example, Clackson et al., (Nature 352:624-628, 1991) and Marks et al., (J. Mol. Biol. 222:581-597, 1991).

In the hybridoma method, a mouse or other appropriate host animal, such as a hamster or macaque monkey, is immunized as herein described to elicit lymphocytes that produce or are capable of producing antibodies that will specifically bind to the tag used for immunization. Alternatively, lymphocytes may be immunized in vitro. Lymphocytes then are fused with myeloma cells using a suitable fusing agent, such as polyethylene glycol, to form a hybridoma cell (Goding, Monoclonal Antibodies: Principles and Practice, pp. 59-103 (Academic Press, 1986)).

The hybridoma cells thus prepared are seeded and grown in a suitable culture medium that preferably contains one or more substances that inhibit the growth or survival of the unfused, parental myeloma cells. For example, if the parental myeloma cells lack the enzyme hypoxanthine guanine phosphoribosyl transferase (HGPRT or HPRT), the culture medium for the hybridomas typically will include hypoxanthine, aminopterin, and thymidine (HAT medium), which substances prevent the growth of HGPRT-deficient cells.

Preferred myeloma cells are those that fuse efficiently, support stable high-level production of antibody by the selected antibody-producing cells, and are sensitive to a medium. Human myeloma and mouse-human heteromyeloma cell lines also have been described for the production of human monoclonal antibodies (see, e.g., Kozbor, J. Immunol., 133: 3001 (1984); Brodeur et al., Monoclonal Antibody Production Techniques and Applications, pp. 51-63, Marcel Dekker, Inc., New York, (1987)). Exemplary murine myeloma lines include those derived from MOP-21 and M.C.-11 mouse tumors available from the Salk Institute Cell Distribution Center, San Diego, Calif. USA, and SP-2 or X63-Ag8-653 cells available from the American Type Culture Collection, Rockville, Md. USA.

Culture medium in which hybridoma cells are growing is assayed for production of monoclonal antibodies directed against the tag. Preferably, the binding specificity of monoclonal antibodies produced by hybridoma cells is determined by immunoprecipitation or by an in vitro binding assay, such as radioimmunoassay (RIA) or enzyme-linked immunoabsorbent assay (ELISA). The binding affinity of the monoclonal antibody can, for example, be determined by Scatchard analysis (see, e.g., Munson et al., Anal. Biochem., 107:220 (1980)).

After hybridoma cells are identified that produce antibodies of the desired specificity, affinity, and/or activity for the tag, the clones may be subcloned by limiting dilution procedures and grown by standard methods (see, e.g., Goding, Monoclonal Antibodies: Principles and Practice, pp. 59-103 (Academic Press, 1986)). Suitable culture media for this purpose include, for example, DMEM or RPMI-1640 medium. In addition, the hybridoma cells may be grown in vivo as ascites tumors in an animal. The monoclonal antibodies secreted by the subclones are suitably separated from the culture medium, ascites fluid, or serum by conventional immunoglobulin purification procedures such as, for example, protein A-Sepharose, hydroxylapatite chromatography, gel electrophoresis, dialysis, or affinity chromatography The disclosure also provides isolated nucleic acid encoding antibodies of the invention, optionally operably linked to control sequences recognized by a host cell, vectors and host cells comprising the nucleic acids, and recombinant techniques for the production of the antibodies, which may comprise culturing the host cell so that the nucleic acid is expressed and, optionally, recovering the antibody from the host cell culture or culture medium. Various systems and methods for antibody production are reviewed by Birch & Racher (Adv. Drug Deliv. Rev. 671-685 (2006)).

For recombinant production of the antibody, the nucleic acid encoding it is isolated and inserted into a replicable vector for further cloning (amplification of the DNA) or for expression. DNA encoding the monoclonal antibody is readily isolated and sequenced using conventional procedures (e.g., by using oligonucleotide probes that are capable of binding specifically to genes encoding the heavy and light chains of the antibody). Many vectors are available. The vector components generally include, but are not limited to, one or more of the following: a signal sequence, an origin of replication, one or more selective marker genes, an enhancer element, a promoter, and a transcription termination sequence.

Suitable host cells for cloning or expressing the DNA encoding the monoclonal antibody and methods for purification of the antibody are described throughout the disclosure.

Recovery of Proteins of Interest Linked to Triple Tag Sequence

The present disclosure provides methods for detecting, including recovering one or more replicable genetic packages expressing a protein of interest specific for a binding partner from an extract, by expressing a protein of interest operably linked to a triple tag sequence that comprises 6× histidine (SEQ ID NO: 1), c-myc (SEQ ID NO: 2) and V5 (SEQ ID NO: 3); screening the replicable genetic packages for binding to antibodies specific 6× histidine (SEQ ID NO: 1), c-myc (SEQ ID NO: 2) or V5 (SEQ ID NO: 3); and recovering replicable genetic packages that bind to the antibody.

The triple tag sequence can be further used to isolate (e.g. purify) a protein of interest linked to the tag away from other cellular material. For example, by immunoprecipitation, or by using anti-tag antibody affinity columns or anti-tag antibody conjugated beads. When a 6×-histidine tag is used, isolation can be performed using a metal-chelate column (see, e.g., Hochuli in Genetic Engineering: Principles and Methods ed. J K Setlow, Plenum Press, NY, chp 18, pp 87-96). Example 6 shows isolation of an exemplary triple-tagged protein using an exemplary matrix (e.g., a nickel column).

The inclusion of three affinity tags allows up to three consecutive affinity purification steps, thus achieving much higher purification than could be achieved by a single or double tag.

The present disclosure also provides methods for quantifying the amount of tagged protein recovered, isolated or purified. Such methods are useful for e.g. measuring the efficiency of purification processes.

Capture of Proteins of Interest Linked to Triple Tag Sequence

Proteins of interest, including antibodies (e.g., single chain antibodies, single domain antibodies or Fabs or peptides (e.g., non-antibody peptides)) linked to triple tag sequences may be captured (e.g., immobilized) on a surface using a capture agent specific for one or more components of the tag. This enables capture of the tagged protein without the need for a specific binding partner of the protein, e.g. in the case of an antibody, antigen-independent capture of the antibody is enabled.

Examples of surfaces encompassed herein include those formed partially or entirely of glass (e.g., controlled pore glass), polysaccharides (e.g., agarose), polyacrylamides, polystyrene, polyvinyl alcohol, silicones metal, metal-alloy, anopol, polymers, nylon, or microarrays such as protein chips. In certain embodiments, depending on the context, the surface can comprise the well of an assay plate, a filter, a membrane, a chromatographic resin, or a bead. This term also includes a discontinuous solid phase of discrete particles, such as those described in U.S. Pat. No. 4,275,149, and cell surfaces. Adherent or suspension cell surfaces may be used. Primary cell cultures, cell lines or engineered cell lines may be used. Suitable cell types may include: CHO, IM-9, HEK 293, and 3T3. The cells may be fixed, e.g. with formaldehyde, or unfixed.

In some embodiments, a protein of interest linked to a triple tag sequence is captured on a surface by coating or expressing on the surface any 6× histidine, c-myc or V5 capture agent known in the art, including but not limited to: antibodies to histidine, c-myc or V5 such as commercially available anti-tag antibodies (e.g., mouse monoclonal anti-V5 antibody (Invitrogen, catalog number R960-25); anti-V5 antibody (Invitrogen, catalog number 460705); mouse anti-V5 antibody (Zymed, catalog number 37-7500); mouse anti-V5 antibody (Accurate Chemical, catalog number MCA1360GA); mouse anti-V5 antibody, clone V5.J9 (Abcam, catalog number ab60188-100); mouse anti-6× his tag antibody, clone 3H2201 (Abcam, catalog number ab15145-50); rabbit polyclonal anti-V5 antibody (Abcam, catalog number ab9116-100); rabbit anti-V5 antibody (Chemicon, catalog number AB3792); chicken anti-V5 antibody (Abcam, catalog number ab9113-100); anti-c-myc mouse monoclonal antibody (9E10) (Roche, catalog number 11667149001); mouse monoclonal anti-c-myc antibody (Zymed, catalog number 13-2500); mouse monoclonal anti-penta-his antibody (Quiagen, catalog number 34660); mouse anti-6×his antibody, clone AD1.1.10 (R&D Systems, catalog number MAB050)) and matrixes such as metal chelating or other matrixes that bind to a 6× histidine, c-myc or V5 tag including commercially available copper or nickel columns. Once captured, the protein is suitable for testing in assays, e.g. binding assays, including high-throughput assays. Such assays can be used to measure activity and/or quantity of the tagged protein.

Various formats and techniques for binding assays are well known in the art and include, for example, immobilization to filters such as nylon or nitrocellulose; two-dimensional arrays, enzyme linked immunosorbant assay (ELISA), radio-immuno-assay (RIA), competitive binding assays, direct and indirect sandwich assays, immunoprecipitation assays, fluorimetric microvolume assay technology (FMAT™), Luminex™ system assays, fluorescent resonance energy transfer (FRET), bioluminescence resonance energy transfer (BRET), electroimmunoassays, AlphaScreen™, nanoparticle-derived techniques, and surface plasmon resonance (SPR).

Binding assays may be homogeneous or semi-homogeneous. A homogeneous assay is an assay where all the components are mixed together, incubated, and then analyzed. A semi-homogeneous assay is one where the majority of the reaction takes place as a complex mixture, but a washing step is required prior to the addition of a final reagent and analysis, in contrast to a typical stepwise assembly sandwich assay where each component is added then washed off before the next component is added. In some embodiments the assay is an immunoassay. In certain embodiments the assay is a semi-homogeneous Enzyme Immuno-Assay (EIA), Competitive binding assays rely on the ability of a labeled standard (e.g., an antigen or a fragment thereof to which a polypeptide binding agent binds) to compete with antigen in the test sample for binding to the polypeptide binding agent. The amount of antigen in the test sample is inversely proportional to the amount of standard that becomes bound to the antibodies. To facilitate determining the amount of standard that becomes bound, the antibodies typically are insolubilized before or after the competition, so that the bound antigen may conveniently be separated from the unbound antigen. In alternative embodiments, competitive binding assays measure the ability of a labeled polypeptide binding agent to compete with unlabeled polypeptide binding agent for binding to antigen or a fragment thereof.

Sandwich assays typically involve the use of two antibodies, each capable of binding to a different immunogenic portion, or epitope, of the protein to be detected and/or quantitated. In a sandwich assay, the analyte in the test sample is typically bound by a first polypeptide binding agent which is immobilized on a solid phase, and thereafter a second polypeptide binding agent binds to the analyte, thus forming an insoluble three-part complex (see, e.g., U.S. Pat. No. 4,376,110). The second polypeptide binding agent may itself be labeled with a detectable moiety (direct sandwich assays) or may be measured using an anti-immunoglobulin antibody that is labeled with a detectable moiety (indirect sandwich assays). For example, one type of sandwich assay is an enzyme-linked immunosorbent assay (ELISA), in which case the detectable moiety is an enzyme (see, e.g., chapter 18, Current Protocols in Molecular Biology, Ausubel et al., eds., John Wiley & Sons, New York, N.Y. (1995)).

For example, the FMAT™ (fluorimetric microvolume assay technology; Applied Biosystems, Foster City, Calif.) system could use tagged protein bound to beads with either a fluorescently labeled or biotinylated ligand. This has the potential to be run as a completely homogeneous assay format. A virtually identical format could be employed using the Luminex™ system (Luminex Corp., Austin, Tex.) where a similar bead based system is used. The main difference between the FMAT™ and Luminex™ assay formats is in the method of detection. The Luminex™ platform flows the beads through an optical flow cell to measure fluorescent emission from the beads and the FMAT™ images the fluorescence in a narrow plane very near the base of the well of the microplate. Alternatively electrochemiluminescence systems would be readily applicable to screening for affinity modulators due to their high sensitivity and homogenous capacity. These systems, such as the Tricorder™ (BioVeris Corp., Washington D.C.) or the MesoScale Discovery Multi-spot Assay System (Meso Scale Discovery, Gaithersburg, Md.) use ruthenium derived electrochemiluminescent detection technologies. The assay formats that could be optimized for this system would be very similar to the other systems with the primary difference being the use of electrochemiluminescent labeling technology and detection instrumentation.

Yet another example of an assay method involves fluorescent resonance energy transfer (FRET) emissions. For example, one compound is labeled with a FRET donor molecule and its binding partner is labeled with a FRET acceptor molecule, or vice versa. When binding occurs between the binding partners, the FRET donor and FRET acceptor molecules are brought into proximity and emit fluorescence at a certain wavelength. A narrow band pass filter can be used to block all wavelengths except that of the label. FRET molecule pairs are commercially available in the art (e.g., from Invitrogen), and may be used according to the manufacturer's protocol. FRET emissions are detected using optical imaging techniques, such as a CCD camera.

A further example of an assay method is bioluminescence resonance energy transfer (BRET), for example using biosensors as described in WO/06086883.

Another type of assay involves labeling with an electron donor. One molecule is labeled with an electron donor and the interacting molecule is bound to an electrical contact, or vice versa. When binding occurs between the binding partners, the label donates electrons to the electrical contact (see, e.g., Ghindilis, Biochem Soc Trans. 28:84-9, (2000); and Dai et al., Cancer Detect Prey. 29:233-40 (2005), which describe methods for electro immunoassays). The electron contact would then be read by an A to D (analog to digital) converter and quantified. The higher the electron count the more interactions took place.

An additional example of an assay method is AlphaScreen™ (PerkinElmer, Waltham, Mass.) which employs a bead-based chemistry to study biomolecular interactions in a microplate format. It is a non-radioactive, homogeneous proximity assay whereby binding of molecules captured on the beads leads to an energy transfer from one bead to the other, ultimately producing a luminescent/fluorescent signal (see, e.g., Seethala & Prabhavathi, Homogeneous Assays AlphaScreen Handbook of Drug Screening. Marcel Dekker Pub., 2001, pp. 106-110).

Molecular interactions may also be detected using nanoparticle-derived techniques (see, e.g., Ao et al., Anal Chem. 78:1104-6 (2006), which describes gold nanoparticle quenching; Tang et al., Biosens Bioelectron. 2005 Nov. 30, which describes SiO(2)/Au nanoparticle surfaces in antibody detection; and Lieu et al., J Immunol Methods. 307:34-40 (2005), which describes silicon dioxide nanoparticles containing dibromofluorescein for use in solid substrate-room temperature phosphorescence immunoassay (SS-RTP-IA)).

One embodiment of a label capable of single molecule detection is the use of plasmon-resonant particles (PRPs) as optical reporters, as described in Schultz et al., Proc. Natl. Acad. Sci. USA 97:996-1001 (2000). PRPs are metallic nanoparticles, e.g. 40-100 nm in diameter, which scatter light because of a collective resonance of the conduction electrons in the metal (the surface plasmon resonance). The magnitude, peak wavelength, and spectral bandwidth of the plasmon resonance associated with a nanoparticle are dependent on the particle's size, shape, and material composition, as well as the local environment. By influencing these parameters during preparation, PRPs can be formed that have scattering peak anywhere in the visible range of the spectrum. For spherical PRPs, both the peak scattering wavelength and scattering efficiency increase with larger radius, providing a means for producing differently colored labels. Populations of silver spheres, for example, can be reproducibly prepared for which the peak scattering wavelength is within a few nanometers of the targeted wavelength, by adjusting the final radius of the spheres during preparation. Because PRPs are bright, yet nanosized, they are used as indicators for single-molecule detection; that is, the presence of a bound PRP in a field of view can indicate a single binding event. An example of a surface plasmon resonance detector system is the BIAcore assay system (see, e.g., Malmquist, J Molec Recognition, 7:1-7 (1994)). Proteins of interest, including for example single chain antibodies, linked to a triple tag sequence of the present disclosure may be detected and their affinity for a binding partner (e.g., an antigen) measured through surface plasmon resonance (SPR). This method is based on the phenomenon which occurs when surface plasmon waves are excited at a metal/liquid interface. Light is directed at, and reflected from, the side of the surface not in contact with sample, and SPR causes a reduction in the reflected light intensity at a specific combination of angle and wavelength. Biomolecular binding events cause changes in the refractive index at the surface layer, which are detected as changes in the SPR signal. The binding event can be either binding association or disassociation between a receptor-ligand pair. The changes in refractive index can be measured essentially instantaneously and therefore allows for determination of the individual components of an affinity constant. More specifically, the method enables accurate measurements of association rates ($k_{on}$) and disassociation rates (koff). Methods for measuring binding affinity, including association and disassociation rates using surface plasmon resonance are well known in the arts and can be found described in, for example, Jonsson and Malmquist, Advances in Biosensors, 2:291-336 (1992) and Wu et al. Proc. Natl. Acad. Sci. USA, 95:6037-6042 (1998).

Example 5 describes exemplary SPR assays performed by passing antigen over tagged scFv's captured on an anti-V5 surface or an anti his surface.

Many recombinant proteins available for use in assays are expressed as a fusion with a single tag, commonly 6× histidine, for ease of purification and are provided or sold with the tag still present. Triple-tagged proteins can advantageously be used in assays containing such single-tagged proteins without interference with the assay results, since the two alternative tags e.g. c-myc and V5 tag can be used for capture and detection.

Detection of Proteins of Interest Linked to Triple Tag Sequence

Tags that comprise an epitope for an antibody can be detected either in vivo or in vitro using anti-tag antibodies that are conjugated to a detectable marker. The detectable marker can be any one which is capable of producing, either directly or indirectly, a measurable signal, such as a radioactive, chromogenic, luminescence, or fluorescent signal, which can be used to quantitate the amount of bound detectable moiety or label in a sample. Detectable labels known in the art include radioisotopes, such as 3H, 14C, 32P, 35S, or 125I, electrochemiluminescent labels (such as Ruthenium (Ru)-based catalyst in conjunction with substrates, etc.), luminescent or bioluminescent labels (e.g., Europium, Vanadium), fluorescent or chemiluminescent compounds, such as fluorescein isothiocyanate, rhodamine, or luciferin, enzymes (e.g., enzyme, such as alkaline phosphatase, β-galactosidase, or horseradish peroxidase), colorimetric labels such as colloidal gold, colored glass or plastic beads (e.g., polystyrene, polypropylene, latex, etc.), paramagnetic atoms or magnetic agents, electron-dense reagents, a nano- or micro-bead containing a fluorescent dye, nanocrystals, a quantum dot, a quantum bead, a nanotag, dendrimers with a fluorescent label, a micro-transponder, an electron donor molecule or molecular structure, or a light reflecting particle. the microparticles may be nanocrystals or quantum dots. Nanocrystals are substances that absorb photons of light, then re-emit photons at a different wavelength (fluorophores). In addition, additional florescent labels, or secondary antibodies may be conjugated to the nanocrystals. Nanocrystals are commercially available from sources such as Invitrogen and Evident Technologies (Troy, N.Y.). Other labels include E)-5-[2-(methoxycarbonyl)ethenyl]cytidine, which is a nonfluorescent molecule that when subjected to ultraviolet (UV) irradiation yields a product, 3-.beta.-D-ribofuranosyl-2,7-dioxopyrido[2,3-d]pyrimidine, which displays a strong fluorescence signal. Bar code labels are described in U.S. Patent Publication No. US 20070037195.

There are many commercially available antibodies to tags, such as c-myc, HA, VSV-G, HSV, V5, histidine, and FLAG. In addition, antibodies to tags used in the disclosure can be produced using standard methods to produce antibodies, as described above and including, for example, by monoclonal antibody production (Campbell, A. M., Monoclonal Antibodies Technology: Laboratory Techniques in Biochemistry and Molecular Biology, Elsevier Science Publishers, Amsterdam, the Netherlands (1984); St. Groth et al., J. Immunology. 35: 1-21 (1990); and Kozbor et al., Immunology Today 4:72 (1983)). The anti-tag antibodies can then be detectably labeled through the use of radioisotopes, affinity labels (such as biotin, avidin, etc.), enzymatic labels (such as horseradish peroxidase, alkaline phosphatase, etc) using methods well known in the art, such as described in international application WO 00/70023 and (Harlow and Lane (1989) Antibodies, Cold Spring Harbor Laboratory, pp. 1-726).

Detection assays for proteins of interest linked to a triple tag sequence include, but are not limited to, Western Blot analysis, Immunohistochemistry, ELISA, FACS analysis, enzymatic assays, autoradiography and any of the binding assays mentioned herein. Means for performing these assays are well known to those of skill in the art. For example, radiolabels may be detected using photographic film or scintillation counters, fluorescent markers may be detected using a photodetector to detect emitted light. Enzymatic labels are typically detected by providing the enzyme with a substrate and detecting the reaction product produced by the action of the enzyme on the substrate, and calorimetric labels are detected by simply visualizing the colored label.

Detection methods for proteins of interest linked to a triple tag sequence can be direct or indirect and can include, for example, the measurement of light emission, radioisotopes, calorimetric dyes and fluorochromes. Direct detection includes methods that operate without intermediates or secondary measuring procedures to assess the amount of the binding partner bound by the modified antibody variable domain. Such methods generally employ ligands that are themselves labeled by, for example, radioactive, light emitting or fluorescent moieties. In contrast, indirect detection includes methods that operate through an intermediate or secondary measuring procedure. These methods generally employ molecules that specifically react with the binding partner and can themselves be directly labeled or detected by a secondary reagent. For example, a modified antibody variable domain specific for a binding partner can be detected using an antibody capable of interacting with the modified antibody variable domain, again using the detection methods described above for direct detection. Indirect methods can additionally employ detection by enzymatic labels. Moreover, for the specific example of screening for catalytic antibodies, the disappearance of a substrate or the appearance of a product can be used as an indirect measure of binding affinity or catalytic activity.

Quantitation of Proteins of Interest Linked to Triple Tag Sequence

The present disclosure provides methods for quantifying the amount of tagged protein. Quantification of the amount of tagged protein in an assay is useful for example, for validating the quality of display libraries (e.g., phage display libraries). Using the triple tag, the amount of tagged protein can be quantitated in a high-throughput manner without the need for purification or concentration of the sample, or for the presence of the protein's binding partner. Thus, for example, for antibodies, unpurified periplasmic extract samples can be quantitated in an antigen-independent method whereby the sample is captured using one tag and detected using another. Placement of the triple tag at the C-terminus of the protein means that only full length proteins are detected. Thus, the method can be used to determine the percentage and quantities of proteins of interest (e.g., antibodies such as single chain antibodies, single domain antibodies or Fab fragments of antibodies) expressed in a library (e.g., a phage display library).

Quantification of the amount of tagged protein in an assay is also useful, for example, for normalizing the assay results to account for variation in the amount of tagged protein in the assay. Variation in the expression, folding and stability of different proteins, even from the same expression vector, is well-documented. For example, Ewert et al. determined that the thermodynamic stability and yield of soluble scFv fragments varied according to their VH- or VL-gene family and combination thereof (see, e.g., Ewert et al., J. Mol. Biol. 325: 531-553 (2003)). Thus, when screening multiple samples of unpurified tagged proteins (e.g. scFv) in periplasmic extracts, it is useful to be able to normalize the results to account for such variations, allowing the most potent proteins to be identified.

Example 10 shows the quantitation of scFv fragments in a number of samples whereby the sample is captured using the V5 tag and detected using the 6× histidine tag.

Articles of Manufacture

Articles of manufacture, including, for example kits, are provided by the present disclosure. The article of manufacture may comprise a container and a label or package insert on or associated with the container. Suitable containers include, for example, bottles, vials or syringes. The containers may be formed from a variety of materials such as glass or plastic. The container holds one or more polynucleotides and/or vectors of the present disclosure. The label or package insert may include directions for performing affinity based screening of a tagged peptide.

Preferably, the kit further comprises a solid support for the capture reagents, which may be provided as a separate element or on which an antibody specific for one or more antigens of interest are immobilized. Hence, the antibody specific for one or more antigens of interest in the kit may be immobilized on a solid support, or they may be immobilized on such support that is included with the kit or provided separately from the kit. Preferably, the antibody specific for one or more antigens of interest are coated on a microtiter plate. Where the amplifying molecule is an enzyme, the kit will ordinarily include substrates and cofactors required by the enzyme, and where the amplifying molecule is a fluorophore, a dye precursor that provides the detectable chromophore.

The kit also typically contains instructions for carrying out the assay as well as other additives such as stabilizers, washing and incubation buffers, and the like. The components of the kit will be provided in predetermined ratios, with the relative amounts of the various reagents suitably varied to provide for concentrations in solution of the reagents that substantially maximize the sensitivity of the assay. Particularly, the reagents may be provided as dry powders, usually lyophilized, including excipients, which on dissolution will provide for a reagent solution having the appropriate concentration for combining with the sample to be tested.

Without further description, it is believed that one of ordinary skill in the art may, using the preceding description and the following illustrative examples, make and utilize the agents of the present disclosure and practice the claimed methods. The following working examples are provided to facilitate the practice of the present disclosure, and are not to be construed as limiting in any way the remainder of the disclosure.

EXAMPLES

Example 1

Construction of Vectors with Tag Sequences

Vectors containing different positional order of tag sequences (e.g., pXscFv-HV, pXscFv-VH, pXscFv-VHM, pXscFv-HMV and pXscFv-HM) may be constructed using pXSHM as the original template (see, e.g., FIGS. 1-5). Recombinant DNA techniques may be employed to add, remove or re-position tags (e.g., 6× histidine, V5, and/or c-myc) in a vector (e.g., pXHM). In a similar manner, recombinant DNA techniques may be employed to construct other combinations of tag sequences comprising 6× histidine, c-myc and/or V5. For example, a VHM or HMV tag sequences may be constructed by employing recombinant DNA techniques to introduce a V5 tag sequence to the pXSHM vector. In a similar manner, a VH or HV tag sequences may be constructed by removing the c-myc tag sequence from the pXSHM vector. For all constructs the stuffer sequence (S) is removed by digestion of the vector with Sfi1. Any protein (e.g., a scFv) flanked with Sfi1 sites may then be introduced into the vector by recombinant techniques. The structure of an exemplary vector (pXSHMV) for use in the methods of the present disclosure is set forth in FIG. 5. Starting at the f1 ori site and moving clockwise this vector comprises an ampicillin gene (AMP), a pUC origin, a lac promoter, a pelB signal sequence, a stuffer sequence (S) flanked by Sfi I sites, a 6× histidine tag (H), a c-myc tag (M), a V5 tag (V), an amber stop codon, and a pill gene (e.g., a truncated pill gene sequence such as SEQ ID NO: 18).

In an exemplary method, a vector, pXscFv-HMV, containing a single chain (scFv) and a HMV tag sequence was constructed. Briefly, nested primers were designed to introduce a V5 tag in pXSHM. The V5 tag was introduced by overlap extension PCR with primers comprising the V5 sequence. Two sets of primers were designed, one set of primers amplify upstream with modifications at the 3' end (comprising a region of overlap with a V5 tag sequence), and the other set of primers amplify downstream with modifications at the 5' end (comprising a region of overlap with a V5 tag sequence). For example, two sequential amplifications may be needed to build enough overlap for the following step reaction. Once these fragments were gel purified, overlap extension using the external primers gave a single DNA fragment containing the V5 tag sequence. This fragment was then cloned into the original vector template (pXSHM) by means of the flanking restriction sites, such as XhoI and NdeI.

The following oligonucleotides were designed for the construction of the pXSHMV vector: RLMycLinkV5R1 (GTTAGGGATAGGCTTACCTGCGGCCCCATT-CAGATC-CTCTTCTGAGATGAGTTTTTGTTC) (SEQ ID NO: 11); RLLinkV5R2 (CGTAGAATCGAGACCGAG-GAGAGGGTTAGGGATAGGCTTACCTGCG-GCCCCATT) (SEQ ID NO: 12); RLV5For (CCTAAC-CCTCTCCTCGGTCTCGATTC-TACGAATGGGGCCGCATAGGAGGCTAGTTCTGC) (SEQ ID NO: 13); IR26 (For) (GAGTGCGACGGCCTC-GAGCCCGCCC) (SEQ ID NO: 14); and IR30 (Rev) (CAATAGAAAATTCATATGGTTTACC) (SEQ ID NO: 15). For the upstream fragment, oligonucleotides RLMycLinkV5R1 (SEQ ID NO: 11) and IR26 (SEQ ID NO: 14) were used to amplify from pXSHM and generate the N-terminal portion. Since this fragment did not include all the changes needed for the follow up overlap extension, another amplification was performed using this upstream fragment as template and oligonucleotides RLLinkV5R2 (SEQ ID NO: 12) and IR26 (SEQ ID NO: 14). This amplification generated the full length V5 tag at the 3' end of the upstream fragment. For the downstream fragment, oligonucleotides RLV5For (SEQ ID NO: 13) and IR30 (SEQ ID NO: 15) were used to amplify from pXSHM and generate the C-terminal portion. These two fragments, upstream and downstream fragments, were linked by overlap extension using the external oligonucleotides IR26 (SEQ ID NO: 14) and IR30 (SEQ ID NO: 15). These oligonucleotides contain respectively XhoI and NdeI restriction sites which were used to introduce the single fragment into pXSHM to generate pXSHMV.

Once the pXSHMV vector was generated, an amplified scFv insert with flanking SfiI sites was introduced in place of the stuffer (S) DNA portion of the pXSHMV. The following oligonucleotides were used to amplify the scFv from the vector containing it: IL28Sfi_For (5'-TAATTACTCGCGGC-CCAGCCGGCCATGGCCCAGGTCCAGC (SEQ ID NO: 16); and IL28Sfi_Rev (TATATAATATGGCCCCCGAGGC-CGACATAAGAACTCAGGCCGC) (SEQ ID NO: 17). The pXSHMV vector was then subject to restriction endonuclease digestion with Sfi1 and the amplified scFv inserted in place of the stuffer (S) sequence to generate the pXscFv-HMV vector.

Example 2

Detection of Tag Sequences by ELISA

A protein of interest linked (e.g., fused) to tag sequences (e.g., tagged protein) may be screened for those tagged proteins that can be expressed.

In an exemplary method, scFvs linked to a tag sequence were screened by ELISA for those tags that permit expression of the scFv-tag protein. ScFvs linked to HMV, VHM, HV, VH, or HM tag sequences were tested. ScFvs linked to the tag sequences were expressed in TG1 cells. Periplasmic extracts were prepared and tested for binding in an ELISA assay for binding to a plate coated with an antigen. An antibody specific for the 6× histidine tag, an antibody specific for V5 tag or an antibody specific for the c-myc tag were used to recognize the scFv-HMV tagged protein.

The scFv-HMV tagged protein was detected by an antibody specific for 6× histidine, an antibody specific for c-myc and an antibody specific for V5. These data suggested that the tag components of the scFv-HMV tagged protein were accessible to binding with each of the three anti-tag antibodies.

Example 3

Detection of Tag Sequences by Biacore

Additionally or alternatively to the ELISA described in Example 2, a protein of interest linked to tag sequences may be screened by Biacore for those tagged proteins that can be expressed.

In an exemplary method, a scFv linked to various peptide sequences (e.g., HMV, HVM, HV, HM and VH) was expressed from a phagemid vector and periplasmic extracts prepared. The periplasmic extracts were diluted 10-fold into running buffer (HBS-EP+, Biacore cat# BR-1006-69) and injected over a CM5 sensor chip with antigen immobilized according to the manufacturer's recommendations (Biacore, GE-Healthcare). A secondary antibody specific for 6× histidine, c-myc or V5 was then injected over the bound scFvs.

Biacore analysis indicated that scFvs linked to a HMV tag were identified by antibodies specific for any one of the tag components.

Example 4

Detection of Tag Sequences by Western Blot

Additionally or alternatively to Examples 2 and 3, a protein of interest linked to tag sequences may be screened for those tagged proteins that can be expressed.

In an exemplary method, a protein of interest linked to various peptide sequences (e.g., HMV, VHM, HV, HM and VH) was expressed from a phagemid vector, purified and run in a non-reducing gel. Proteins were then transferred to nitrocellulose by standard techniques and probed for immunoreactivity with an antibody specific for a peptide in the tag sequence and that was conjugated to a detectable label.

Western analysis indicated that scFvs linked to a HMV (6× histidine-c-myc-V5) tag were identified by antibodies to any one of the tag components. Similarly, the scFvs linked to a HV or VH tag were detected by an antibody to either V5 or 6× histidine. ScFvs linked to VHM were detected with antibodies directed to the 6× histidine tag and V5 tag. However the c-myc tag was not detected. These data suggest that the HMV tag does not affect detection of the scFv to which it is linked and that each component of the tag is accessible to antibody binding under denaturing conditions.

Example 5

Kinetic Analysis of Protein of Interest Linked to Tag Sequences

Proteins of interest may be linked to various tag sequences (e.g., HMV, VHM, HV, HM and VH) that allows for stable capture by an antibody to the tag sequence. The captured tagged protein can then be analyzed for kinetics of binding interaction with other molecules of interest.

A. Capture via V5 Tag

In an exemplary method, various tagged proteins were captured on an anti-V5 surface, for example, scFv-HMV, scFv-VH, scFv-HV. Each of these tagged proteins tested comprises the same $V_H$ and $V_L$ regions. The following kinetic analyses were carried out using a Biacore 2000. The results of these analyses were compared with the results of a previous kinetic analysis performed with an untagged IgG with the same $V_H$ and $V_L$ regions.

For the scFv evaluations anti-V5 antibody was immobilized on a CM5 sensor chip by amine coupling according to the manufacturer's recommendations (Biacore, GE-Healthcare). Periplasmic extracts containing scFv constructs were diluted into running buffer and injected over the anti-V5 surface, resulting in capture of the tagged scFv on the surface. Buffer blanks and antigen in multiple concentrations were injected. Resulting sensorgrams were analyzed using kinetic analysis software to determine the on-rate and the off-rate (see, e.g., FIG. 6-8).

Figure 9:
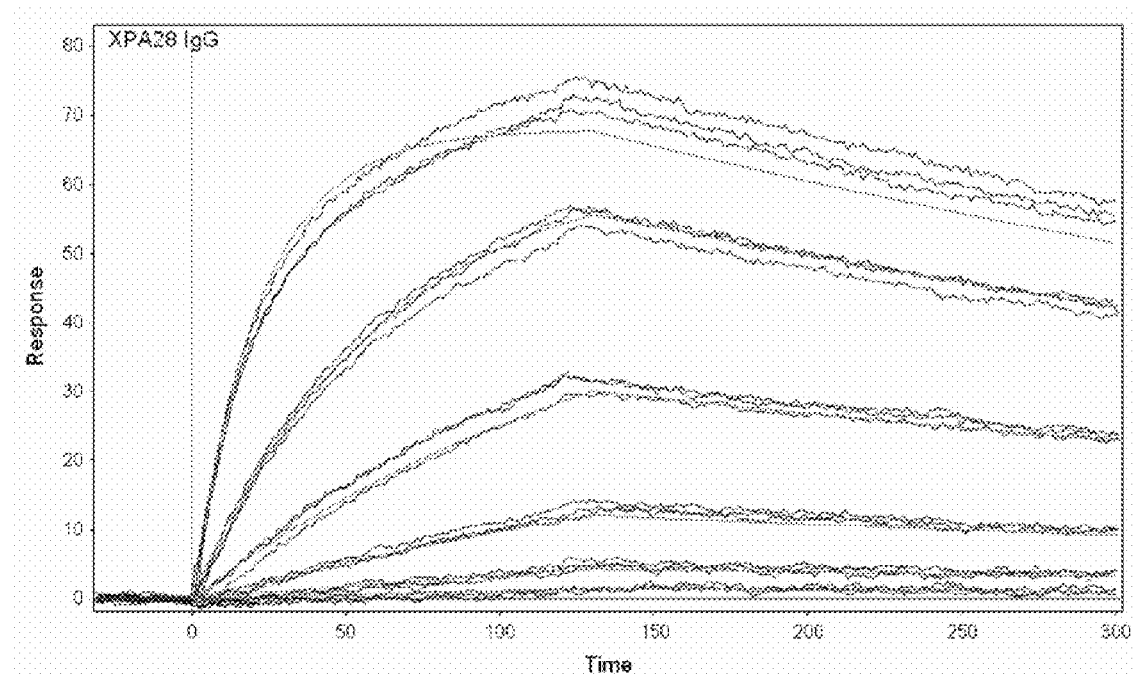
FIG. 9 shows a sensorgram for a kinetic analysis of an exemplary IgG.

Purified IgG was previously evaluated in a similar manner using a Protein A/G capture surface instead of anti-V5. A resulting sensorgram is shown as FIG. 9.

Figure 6:
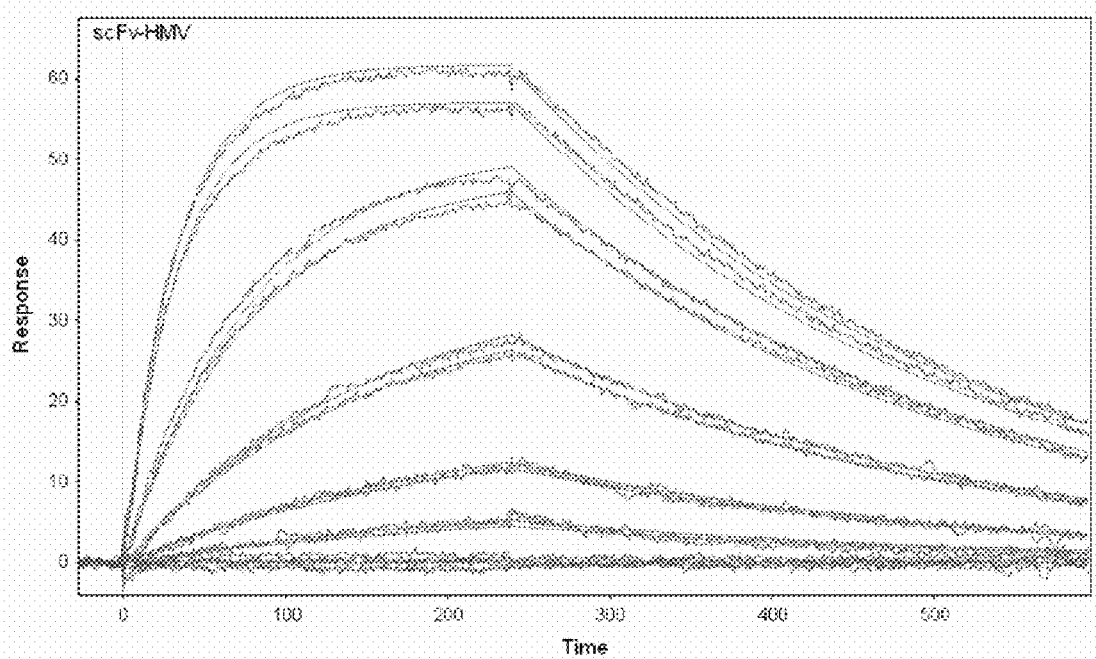
FIG. 6 shows a sensorgram for antigen binding to an exemplary scFv-HMV captured on an anti-V5 surface.
Figure 7:
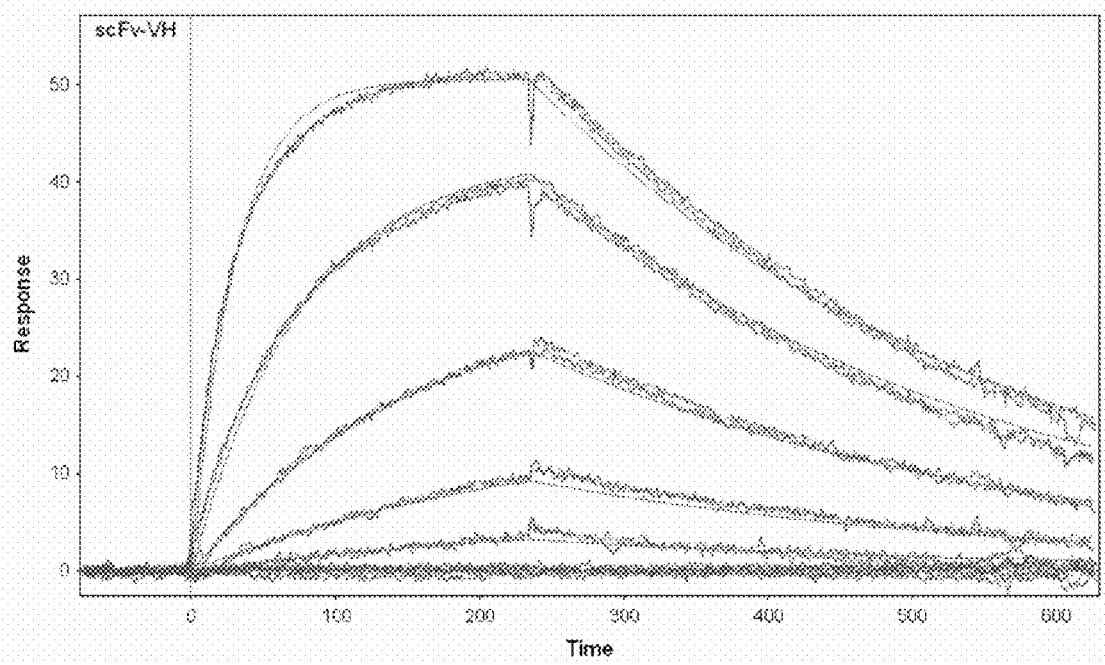
FIG. 7 shows a sensorgram for antigen binding to an exemplary scFv-VH captured on an anti-V5 surface.
Figure 8:
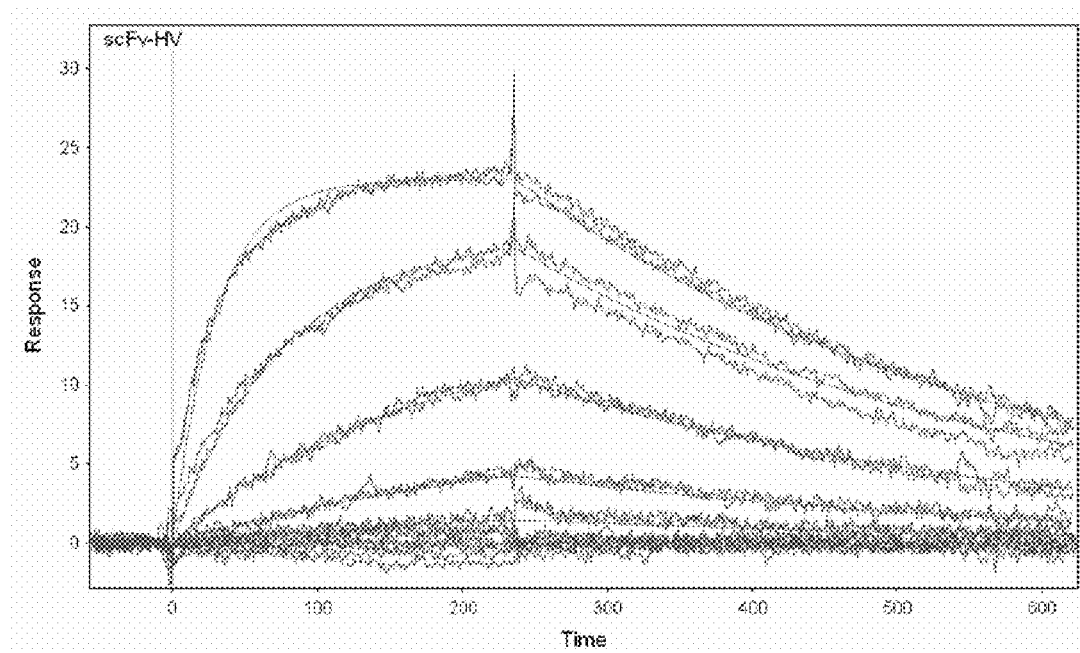
FIG. 8 shows a sensorgram for antigen binding to an exemplary scFv-HV captured on an anti-V5 surface.

The V5 tag sequence enabled stable capture of V5-tagged scFv constructs from periplasmic extracts. Binding of antigen to captured scFv constructs fit well to a 1:1 binding model, which allowed the determination of kinetics of scFv from unpurified extracts (FIGS. 6-8). The values for affinity measured using the anti-V5 capture surface were consistent with values previously measured for the affinity of the IgG version captured by Protein A/G (e.g., $K_D$ of approximately 20 nM). The $K_D$ values for the three scFv constructs shown in Table 1 and the IgG are within experimental error for this methodology, indicating that the V5 capture did not significantly affect the antibody/antigen binding interaction. The ability to measure kinetics of scFv constructs from unpurified samples allows significantly higher throughput of affinity analyses during antibody screening by avoiding the requirement for purification and accurate quantitation of each antibody candidate being evaluated.

TABLE 1

Comparison of affinity measurements for various formats

| Antibody format | On-rate ((M * sec)$^{-1}$) | Off-rate (sec$^{-1}$) | $K_D$ (nM) |
|---|---|---|---|
| scFv-HMV | $1.4 \times 10^5$ | $3.6 \times 10^{-3}$ | 26 |
| scFv-VH | $1.6 \times 10^5$ | $3.0 \times 10^{-3}$ | 19 |
| scFv-HV | $1.6 \times 10^5$ | $2.9 \times 10^{-3}$ | 19 |

B. Capture Via 6× Histidine Tag

In a further exemplary method, HMV tagged scFvs were captured on an anti-6× histidine surface. The kinetic analysis was carried out using a Biacore A100. For the characterization of the scFvs the anti-6× histidine antibody (R&D Systems MAb 050) was immobilized via amine coupling to a series S CM5 sensorchip. Periplasmic extracts containing the scFv constructs were diluted in running buffer and injected over the anti-6× histidine surface, resulting in the capture of the tagged scFv. Buffer blanks and antigen in multiple concentrations were injected over the captured scFv. The resulting sensorgrams were analyzed using kinetic analysis software to determine the on-rate and the off-rate. The 6×-histidine tag sequence enabled capture of the HMV tagged scFv constructs from periplasmic extracts. The captured scFv were able to bind antigen and their on-rate and the off-rates were determined.

Example 6

Nickel Column Purification of a Protein of Interest Linked to Tag Sequences

A protein of interest linked to various peptide sequences (e.g., HMV, VHM, HV, HM and VH) may be purified by any means known in the art.

In an exemplary method, a scFv linked to tag sequences was purified using a nickel column. Briefly, the scFv fused to the triple tag sequence was expressed from a vector (e.g., pXHMA, pXHMVA, pXHVA and pXVHA) in a bacterial system (e.g., TG1 cells). Next, a periplasmic extract was prepared by standard methods and a nickel resin prepared by equilibrating the resin with an appropriate buffer (e.g., PBS+ 300 mM NaCl). The scFv tagged proteins were purified from the periplasmic extract by adding the equilibrated nickel resin to the extract. After incubation, the column was washed and the scFv tagged protein was eluted.

Figure 10:
FIG. 10 shows a SDS-PAGE of an exemplary scFv linked to a multi-tag sequence (e.g., HMV, HV, HM or VH) and purified on a nickel column.

After nickel purification of scFv tagged proteins, tagged proteins with HMV and HV sequences were purified with higher recovery than the scFv tagged proteins comprising VH and HM sequences (FIG. 10).

Example 7

Recovery of Protein of Interest Linked to Tag Sequences

The yield and recovery of a protein of interest operably linked to various peptide sequences (e.g., HMV, VHM, HV, HM and VH) and that binds a binding partner may be determined, for example, by Biacore.

In an exemplary method, yield and recovery of the protein of interest linked to a triple tag sequence was measured using a Biacore 2000 instrument as follows. An antigen was immobilized to a high density (e.g., density at which the binding is mass-transport limited, thus dependent on concentration rather than binding kinetics) on a CM-5 chip. Periplasmic extracts were diluted into running buffer and purified scFv constructs were diluted to an estimated concentration of approximately 1 µg/mL. The samples were filtered and injected. Initial slope was calculated from the association phase of the binding sensorgram using BiaEval Software (Biacore, GE-Healthcare). A conversion factor was calculated using the initial slope for a sample with known concentration and applied to the unknown samples to estimate concentrations. The concentrations and dilutions were then used to estimate yield and percent recovery (Table 2). Of the constructs tested, the scFv linked to the HMV sequence had the highest level of expression and the highest recovery after purification.

TABLE 2

Yield and Percent Recovery of Purified ScFv Constructs

| Construct | Expression yield (µg) | Yield of purified (µg) | % Recovery |
|---|---|---|---|
| pscFv-HM | 160 | 51 | 32 |
| pscFv-HMV | 226 | 174 | 77 |
| pscFv-HV | 145 | 27 | 12 |
| pscFv-VH | 81 | 10 | 19 |

Example 8

Production and Stability of Phage Comprising Tag Sequences

The production and stability of a phage comprising various peptide sequences (e.g., HMV, VHM, HV, HM and VH) may be determined by mock selection followed by phage titer determination and restriction enzyme analysis of the phagemid DNA.

In an exemplary method, the production and stability of various phagemid vectors comprising scFv linked to HMV, HV, or VH peptide sequences was determined. For example, the phagemid constructs were taken separately through a simulated 3 rounds of selection (e.g., rescue, infection, rescue, infection, rescue, infection). At the end, 3 isolates and a pool from the third round for each construct were processed for phagemid purification and restriction endonuclease analysis (e.g., SfiI).

Figure 11:
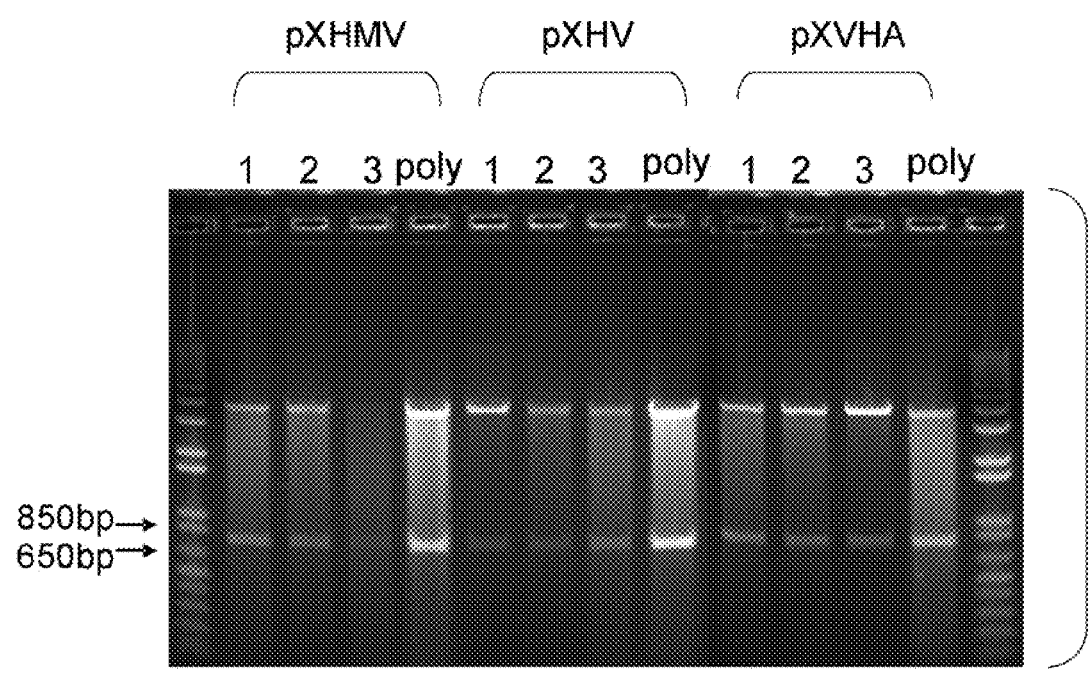
FIG. 11 shows a gel electrophoresis analysis of phagemid DNA from pXHMV, pXHV, and pXVH after 1, 2 and 3 rounds of selection.

The phagemid constructs showed similar phage titer production and same DNA size analysis (see, e.g., FIG. 11). These data suggested that the introduction of the V5 tag, c-myc tag and histidine tag did not affect phage titer production and the integrity of the phagemid DNA.

Example 9

Use of Tag Sequences for Library Screening

Various peptide sequences (e.g., HMV, VHM, HV, HM and VH) may be used to screen a library (e.g., a phagemid library) for a protein of interest. For example, a binding partner for the protein of interest may be used to capture the protein of interest. After capture, the protein of interest may be detected by an antibody to the tag sequence.

In an exemplary method, a large phagemid library (e.g., $10^{11}$) was constructed in the pXscFv-1-IMV vector comprising scFvs. This large scFv-phagemid library was used to select scFvs that bind to a variety of antigens. Antigens included a short peptide, a soluble protein, a cytoplasmic protein and extracellular domains of two different membrane bound proteins. Thousands of different scFvs with HMV sequences were expressed in bacteria and screened by ELISA. Briefly, a periplasmic extract was prepared and added to ELISA plates coated with an antigen. After an incubation, the plates were washed and an antibody specific for the tag sequence (e.g., anti-V5) was added to the wells. A second incubation was performed in the presence of a secondary antibody to detect the anti-V5 antibody. After the incubation the plates were washed and read on a spectrophotometer.

From the screening conducted with the short peptide, soluble protein, cytoplasmic protein and extracellular domains of two membrane bound proteins, a number of unique heavy and light chain pairs were identified. For example, when the screening was performed with the short peptide antigen, 54 unique heavy chain sequences, 55 unique light chain sequences and 60 unique heavy and light chain pairs were identified. When the screening was performed with a soluble protein antigen, 63 unique heavy chain sequences, 45 unique light chain sequences and 74 unique heavy and light chain pairs were identified. When the screening was performed with the cytoplasmic protein antigen, 44 unique heavy chain sequences, 46 unique light chain sequences and 49 unique heavy and light chain pairs were identified. When the screening was performed with the first membrane bound protein antigen, 56 unique heavy chain sequences, 87 unique light chain sequences and 98 unique heavy and light chain pairs were identified. When the screening was performed with the second membrane bound protein antigen, 74 unique heavy chain sequences, 74 unique light chain sequences and 89 unique heavy and light chain pairs were identified. These data suggest that the HMV sequence of the present disclosure may be used in high throughput screening of a library. In another example, scFv-HMV clones in periplasmic extracts were analyzed for kinetics of antigen binding by Biacore using an anti-V5 capture surface. Such antigen binding kinetic analysis of scFv from unpurified preparations is enabled by the use of a stable capture tag such as V5. A stable capture tag refers to one that is bound by an antibody (e.g., anti-V5) with a very slow off-rate (e.g., less than or equal to $1-2 \times 10^{-4}$). The ability to carry out these analyses using periplasmic extracts allows high throughput kinetic screening of scFv libraries. While this type of analysis is currently possible with Fab fragments and IgG molecules due to the presence of constant regions that can be bond by specific antibodies, scFvs, single domain antibodies and other proteins without constant regions previously could not be analyzed in this manner.

Example 10

Determination of Relative Concentration of Peptide of Interest

The capture and detection of a protein of interest linked to various peptide sequences (e.g., HMV, VHM, HV, HM and VH) may be used to determine the relative concentration of a protein of interest (e.g. a scFv) in a periplasmic extract which permits normalization of the protein's functional activity.

In an exemplary method, scFvs in a periplasmic extract were captured through V5 and detected through the 6× histidine tag. The relative concentration of the protein of interest (see, e.g., Table 3) can be used to normalize scFv activity in a functional assay. Such functional assays include, antigen binding competition assays, ligand-receptor blocking assay or cell based signaling assays. Briefly, anti-V5 antibody was immobilized on a 96-well plate. Periplasmic extracts were added to the wells. After incubation, the plates were washed and an antibody to the histidine tag sequence was added. After an incubation, the plates were washed, detection reagents were added, and the plates were read on a spectrophotometer. The results from an exemplary 96-well plate showing the relative concentrations of expressed scFv in periplasmic extracts as determined by ELISA are illustrated in Table 3.

TABLE 3

Relative Concentrations of Exemplary Protein of Interest Determined by ELISA (expressed as fold over background)*

|   | 1   | 2    | 3    | 4    | 5    | 6    | 7    | 8    | 9    | 10   | 11   | 12   |
|---|-----|------|------|------|------|------|------|------|------|------|------|------|
| A | 1.1 | 0.9  | 5.9  | 7.9  | 1.2  | 1    | 3.6  | 2.8  | 15.6 | 12   | 4.2  | 0.9  |
| B | 3.8 | 0.9  | 1.1  | 53.4 | 26.7 | 2.1  | 2.7  | 51.2 | 1.6  | 4.2  | 62.5 | 1.4  |
| C | 6.4 | 1    | 5.3  | 4.6  | 21.5 | 5.1  | 4.3  | 18.4 | 5.5  | 41.6 | 3.1  | 3.5  |
| D | 8.6 | 1.2  | 3.1  | 1.3  | 2.5  | 44.4 | 52.7 | 32.5 | 0.8  | 5    | 2.3  | 1.3  |
| E | 2.6 | 5.2  | 3.5  | 2.8  | 1.8  | 1.4  | 1.1  | 2.3  | 6.1  | 2.1  | 36.3 | 7.3  |
| F | 1.1 | 40.3 | 3.6  | 1.5  | 1.8  | 1.7  | 1.4  | 1.9  | 36.9 | 3.3  | 19.1 | 19.4 |
| G | 2   | 1    | 6.5  | 2.4  | 36   | 6.7  | 2    | 1.3  | 1.2  | 1.9  | 2.8  | 2.3  |
| H | 1.6 | 12.4 | 11.6 | 1.3  | 43.1 | 55.8 | 1.3  | 1    | 28.3 | 1.2  | 1.9  | 40.1 |

*A1 and A2 are negative controls and H12 is a positive control

Example 11

Quantitation of Tagged scFv Fragments in Periplasmic Extracts Using FRET

In an exemplary method, fluorescent resonance energy transfer (FRET) emissions can be used to quantitate unpurified tagged protein samples in solution in a sensitive, high-throughput manner. For example, multiple samples of periplasmic extracts containing scFv are dispensed into a multi-well plate. One tag, for example, V5, or two tags, for example, V5 and c-myc, are detected with, for example, an anti-V5, or, for example, both an anti-V5 and anti-c-myc, antibody labeled with a FRET donor molecule (e.g. yellow fluorescent protein) and another tag e.g. 6× histidine is detected with an antibody labeled with a FRET acceptor molecule (e.g. green fluorescent protein), or vice versa. Binding to the tag components brings the FRET donor and FRET acceptor molecules into proximity (typically 10-100 Å). When the donor fluor is excited, its emission excites the acceptor molecule causing fluorescence at a certain wavelength. A narrow band pass filter can be used to block all wavelengths except that of the label. FRET excitation is weak for labels in solution and the proximity created by binding to the tagged components greatly increases the FRET signal over background. FRET molecule pairs are commercially available in the art. Example pairs include: fluorescein and tetramethylrhodamine; IAEDANS and fluorescein; EDANS and dabcyl; fluorescein and fluorescein; BODIPY FL and BODIPY FL; fluorescein and QSY 7 and QSY 9 dyes (all available from Invitrogen Corp., Carlsbad Calif.), and may be used according to the manufacturer's protocols. FRET emissions are detected using optical imaging techniques, such as a CCD camera. For a review of the FRET technique and assay design see e.g. Osborn J. "A review of radioactive and non-radioactive-based techniques used in life science applications—Part II: High-throughput screening" Life Science News, March 2001, Amersham Pharmacia Biotech.

EMBODIMENTS

1. A nucleic acid library comprising a plurality of polynucleotides, wherein each of the polynucleotides codes for a protein of interest linked to a polynucleotide coding for a triple tag sequence, wherein the triple tag sequence comprises 6× histidine (SEQ ID NO: 1), c-myc (SEQ ID NO: 2) and V5 (SEQ ID NO: 3).
2. The nucleic acid library of embodiment 1, wherein 6× histidine (SEQ ID NO: 1), c-myc (SEQ ID NO: 2) and V5 (SEQ ID NO: 3) are directly linked.
3. The nucleic acid library of embodiment 1, wherein 6× histidine (SEQ ID NO: 1), c-myc (SEQ ID NO: 2) and V5 (SEQ ID NO: 3) are indirectly linked through a spacer.
4. The nucleic acid library of embodiment 3, wherein the spacer is 3 to 7 amino acids in length.
5. The nucleic acid library of embodiment 4, wherein the spacer is GAA or KAA.
6. The nucleic acid library of embodiment 1, wherein the polynucleotide coding for the triple tag sequence is represented by HHHHHHEQKLISEEDLGKPIPNPLLGLDST (SEQ ID NO: 4).
7. The nucleic acid library of embodiment 1, wherein the polynucleotide coding for the triple tag sequence is represented by HHHHHHGAAEQKLISEEDLKAAGKPIPNPLLGLDST (SEQ ID NO: 5).
8. The nucleic acid library of embodiment 1, wherein the polynucleotide coding for the triple tag sequence is:
   (a.) a polynucleotide that is 90% identical to SEQ ID NO: 4 or SEQ ID NO: 5,
   (b.) a polynucleotide that hybridizes under stringent conditions to a polynucleotide represented by SEQ ID NO: 4 or SEQ ID NO: 5; or
   (c.) a polynucleotide that is complementary to SEQ ID NO: 4 or SEQ ID NO: 5.
9. The nucleic acid library of embodiment 1, wherein the polynucleotide of interest is operably linked to one or more expression control elements.
10. The nucleic acid library of embodiment 9, wherein the expression control element is a promoter.
11. The nucleic acid library of embodiment 10, wherein the promoter is a bacterial promoter.
12. The nucleic acid library of embodiment 1, wherein the polynucleotide coding for the protein of interest is operably linked to a polynucleotide coding for a signal sequence.
13. The nucleic acid library of embodiment 12, wherein the signal sequence is MKYLLPTAAAGLLLLAAQPAMA (SEQ ID NO: 7),
14. The nucleic acid library of embodiment 12, wherein the signal sequence is MKILILGIFLFLCSTPAWA (SEQ ID NO: 8).
15. The nucleic acid library of embodiment 12, wherein the signal sequence is MRTLAILAAILLVALQAQA (SEQ ID NO: 9).
16. The nucleic acid library of embodiment 12, wherein the signal sequence is MGALAVFAVACLAAVASVAHA (SEQ ID NO: 10).
17. The nucleic acid library of embodiment 1, wherein the polynucleotide of interest codes for a binding molecule or fragment thereof.

18. The nucleic acid library of embodiment 17, wherein the binding molecule is an antibody or fragment thereof.
19. The nucleic acid library of embodiment 18, wherein the binding molecule is a single chain antibody, a single domain antibody or a Fab fragment of an antibody.
20. The nucleic acid library of embodiment 18, wherein the binding molecule is selected from the group consisting of Fab, Fab', Fab'-SH, Fv, scFv, and a F(ab')$_2$.
21. The nucleic acid library of embodiment 18, wherein the binding molecule comprises 5' to 3', $V_H$-Linker-$V_L$ or $V_L$-Linker-$V_H$ wherein the linker sequence is ASTGGGGSGGGGSGGGGS (SEQ ID NO: 6) and wherein the triple tag sequence is represented by SEQ ID NO: 5.
22. The nucleic acid library of embodiment 1, wherein the 5' end of the polynucleotide coding for the triple tag sequence is operably linked to the 3' end of the polynucleotide of interest.
23. A bacteriophage library comprising a plurality of phage displaying a plurality of polypeptides, wherein each polypeptide comprises a protein of interest linked to a triple tag sequence, wherein the triple tag sequence comprises 6× histidine (SEQ ID NO: 1), c-myc (SEQ ID NO: 2) and V5 (SEQ ID NO: 3).
24. The bacteriophage library of embodiment 23, wherein 6× histidine (SEQ ID NO: 1), c-myc (SEQ ID NO: 2) and V5 (SEQ ID NO: 3) are directly linked.
25. The bacteriophage library of embodiment 23, wherein 6× histidine (SEQ ID NO: 1), c-myc (SEQ ID NO: 2) and V5 (SEQ ID NO: 3) are indirectly linked through a spacer.
26. The bacteriophage library of embodiment 25, wherein the spacer is 3 to 7 amino acids in length.
27. The bacteriophage library of embodiment 26, wherein the spacer is GAA or KAA.
28. The bacteriophage library of embodiment 23, wherein the polynucleotide coding for the triple tag sequence is represented by HHHHHHEQKLISEEDLGKPIPNPLLGLDST (SEQ ID NO: 4).
29. The bacteriophage library of embodiment 23, wherein the polynucleotide coding for the triple tag sequence is represented by HHHHHHGAAEQKLISEEDLKAAGKPIPNPLLGLDST (SEQ ID NO: 5).
30. The bacteriophage library of embodiment 23, wherein the protein of interest codes for a binding molecule or fragment thereof.
31. The bacteriophage library of embodiment 30, wherein the binding molecule is an antibody or fragment thereof.
32. The bacteriophage library of embodiment 31, wherein the binding molecule is a single chain antibody, a single domain antibody or a Fab fragment of an antibody.
33. The bacteriophage library of embodiment 31, wherein the binding molecule is selected from the group consisting of Fab, Fab', Fab'-SH, Fv, scFv, and a F(ab')$_2$.
34. The bacteriophage library of embodiment 23, wherein the protein of interest comprises 5' to 3', $V_H$-Linker-$V_L$ or $V_L$-Linker-$V_H$ wherein the linker sequence is ASTGGGGSGGGGSGGGGS (SEQ ID NO: 6) and wherein the triple tag sequence is represented by SEQ ID NO: 5.
35. The bacteriophage library of embodiment 23, wherein the 5' end of the polynucleotide coding for the triple tag sequence is operably linked to the 3' end of the polynucleotide of interest.
36. A vector comprising a polynucleotide coding for a protein of interest linked to a polynucleotide coding for a triple tag sequence, wherein the triple tag sequence comprises 6× histidine (SEQ ID NO: 1), c-myc (SEQ ID NO: 2) and V5 (SEQ ID NO: 3).
37. The vector of embodiment 36, wherein 6× histidine (SEQ ID NO: 1), c-myc (SEQ ID NO: 2) and V5 (SEQ ID NO: 3) are directly linked.
38. The vector of embodiment 36, wherein 6× histidine (SEQ ID NO: 1), c-myc (SEQ ID NO: 2) and V5 (SEQ ID NO: 3) are indirectly linked through a spacer.
39. The vector of embodiment 38, wherein the spacer is 3 to 7 amino acids in length.
40. The vector of embodiment 39, wherein the spacer is GAA or KAA.
41. The vector of embodiment 36, wherein the polynucleotide coding for the triple tag sequence is represented by HHHHHHEQKLISEEDLGKPIPNPLLGLDST (SEQ ID NO: 4).
42. The vector of embodiment 36, wherein the polynucleotide coding for the triple tag sequence is represented by HHHHHHGAAEQKLISEEDLKAAGKPIPNPLLGLDST (SEQ ID NO: 5).
43. The vector of embodiment 36, wherein the polynucleotide coding for the triple tag sequence is:
  (a.) a polynucleotide that is 90% identical to SEQ ID NO: 4 or SEQ ID NO: 5,
  (b.) a polynucleotide that hybridizes under stringent conditions to a polynucleotide represented by SEQ ID NO: 4 or SEQ ID NO: 5; or
  (c.) a polynucleotide that is complementary to SEQ ID NO: 4 or SEQ ID NO: 5.
44. The vector of embodiment 36, wherein the polynucleotide of interest is operably linked to one or more expression control elements.
45. The vector of embodiment 44, wherein the expression control element is a promoter.
46. The vector of embodiment 45, wherein the promoter is a bacterial promoter.
47. The vector of embodiment 36, wherein the polynucleotide coding for the protein of interest is operably linked to a polynucleotide coding for a signal sequence.
48. The vector of embodiment 47, wherein the signal sequence is MKYLLPTAAAGLLLLAAQPAMA (SEQ ID NO: 7),
49. The vector of embodiment 47, wherein the signal sequence is MKILILGIFLFLCSTPAWA (SEQ ID NO: 8).
50. The vector of embodiment 47, wherein the signal sequence is MRTLAILAAILLVALQAQA (SEQ ID NO: 9).
51. The vector of embodiment 47, wherein the signal sequence is MGALAVFAVACLAAVASVAHA (SEQ ID NO: 10).
52. The vector of embodiment 36, wherein the polynucleotide of interest codes for a binding molecule or fragment thereof.
53. The vector of embodiment 52, wherein the binding molecule is an antibody or fragment thereof.
54. The vector of embodiment 52, wherein the binding molecule is a single chain antibody, a single domain antibody or a Fab fragment of an antibody.
55. The vector of embodiment 53, wherein the binding molecule is selected from the group consisting of Fab, Fab', Fab'-SH, Fv, scFv, and a F(ab')$_2$.
56. The vector of embodiment 55, wherein the protein of interest comprises 5' to 3', $V_H$-Linker-$V_L$, wherein the linker sequence is ASTGGGGSGGGGSGGGGS (SEQ ID NO: 6).

57. The vector of embodiment 36, wherein the 5' end of the polynucleotide coding for the triple tag sequence is operably linked to the 3' end of the polynucleotide of interest.

58. A host cell comprising the vector of any one of embodiments 36-57.

59. A method of producing a protein of interest linked to a triple tag sequence comprising culturing the host cell of embodiment 58 under conditions wherein the polynucleotide sequences are expressed and the protein of interest linked to the triple tag sequence is produced.

60. The method of embodiment 59 further comprising recovering the protein from the host cell culture.

61. A tagged protein comprising a protein of interest linked to a triple tag sequence comprising 6× histidine (SEQ ID NO: 1), c-myc (SEQ ID NO: 2) and V5 (SEQ ID NO: 3).

62. The tagged protein of embodiment 61, wherein the 6× histidine (SEQ ID NO: 1), c-myc (SEQ ID NO: 2) and V5 (SEQ ID NO: 3) are directly linked.

63. The tagged protein of embodiment 61, wherein the 6× histidine (SEQ ID NO: 1), c-myc (SEQ ID NO: 2) and V5 (SEQ ID NO: 3) are indirectly linked through a spacer.

64. The tagged protein of embodiment 63, wherein the spacer is 3 to 7 amino acids in length.

65. The tagged protein of embodiment 64, wherein the spacer is GAA or KAA.

66. The tagged protein of embodiment 62, wherein the triple tag sequence is represented by HHHHHHEQKLISEEDLGKPIPNPLLGLDST (SEQ ID NO: 4).

67. The tagged protein of embodiment 63, wherein the triple tag sequence is represented by HHHHHHGAAEQKLISEEDLKAAGKPIPNPLLGLDST (SEQ ID NO: 5).

68. The tagged protein of embodiment 61, wherein the triple tag sequence is 70% identical to SEQ ID NO: 4 or SEQ ID NO: 5.

69. The tagged protein of embodiment 61, wherein the triple tag sequence is 80% identical to SEQ ID NO: 4 or SEQ ID NO: 5.

70. The tagged protein of embodiment 61, wherein the triple tag sequence is 90% identical to SEQ ID NO: 4 or SEQ ID NO: 5.

71. A method of capturing a tagged protein, said method comprising:
(a.) preparing a periplasmic extract from the host cell of embodiment 58; and
(b.) contacting the periplasmic extract with an antibody to 6× histidine, c-myc or V5,
wherein the tagged protein is captured by the antibody to 6× histidine, c-myc or V5.

72. A method for recovering a tagged protein, said method comprising:
(a.) preparing a periplasmic extract from the host cell of embodiment 58;
(b.) contacting the periplasmic extract with an antibody to 6× histidine, c-myc or V5 or with a nickel column, wherein the tagged protein binds to the antibody to 6× histidine, c-myc or V5 or to a nickel column;
(c.) eluting tagged protein bound to antibody or the column; and
(d.) recovering the tagged protein from the eluate.

73. A method of screening a phagemid library of proteins of interest, wherein the library comprising a plurality of vectors according to embodiment 36, said method comprising:
(a.) expressing a plurality of polynucleotides from the plurality of vectors according to embodiment 36;
(b.) screening the expressed polynucleotides for binding to an antibody specific for V5, c-myc or 6× histidine; and
(c.) recovering the expressed polynucleotides that are bound in step (b.).

74. A polypeptide library comprising a plurality of polypeptides according to any one of embodiments 61-70.

75. A library of bacteriophage displaying on their surface a polypeptide according to any one of embodiments 61-70.

76. A method for selecting from a plurality of polypeptides, the polypeptides that bind to an antigen, the method comprising:
(a) contacting the polypeptide library of embodiment 74 or embodiment 75 with an antigen; and
(b) selecting the polypeptides that bind to the antigen.

77. A method for selecting from a plurality of polypeptides, polypeptides that bind to an antigen, the method comprising:
(a) expressing the library of embodiment 1 to produce the plurality of polypeptides; and
(b) contacting the expressed polypeptides with the antigen; and
(c) selecting polypeptides that bind to the antigen.

78. A plurality of vectors, wherein each vector in the plurality of vectors comprises a polynucleotide coding for a protein of interest linked to a polynucleotide coding for a triple tag sequence, wherein the triple tag sequence comprises 6× histidine (SEQ ID NO: 1), c-myc (SEQ ID NO: 2) and V5 (SEQ ID NO: 3).

79. A plurality of vectors according to any one of embodiments 36-57 or any combination thereof.

80. A library of single chain antibodies, wherein the single chain antibody is linked to a triple tag sequence comprising 6× histidine (SEQ ID NO: 1), c-myc (SEQ ID NO: 2) and V5 (SEQ ID NO: 3).

81. The library of embodiment 80, wherein the 6× histidine (SEQ ID NO: 1), c-myc (SEQ ID NO: 2) and V5 (SEQ ID NO: 3) are directly linked.

82. The library of embodiment 80, wherein the 6× histidine (SEQ ID NO: 1), c-myc (SEQ ID NO: 2) and V5 (SEQ ID NO: 3) are indirectly linked through a spacer.

83. The library of embodiment 82, wherein the spacer is 3 to 7 amino acids in length.

84. The library of embodiment 83, wherein the spacer is GAA or KAA.

85. The library of embodiment 81, wherein the triple tag sequence is represented by HHHHHHEQKLISEEDLGKPIPNPLLGLDST (SEQ ID NO: 4).

86. The library of embodiment 82, wherein the triple tag sequence is represented by HHHHHHGAAEQKLISEEDLKAAGKPIPNPLLGLDST (SEQ ID NO: 5).

87. A library of Fab fragments, wherein the Fab fragment is linked to a triple tag sequence comprising 6× histidine (SEQ ID NO: 1), c-myc (SEQ ID NO: 2) and V5 (SEQ ID NO: 3).

88. The library of embodiment 87, wherein the 6× histidine (SEQ ID NO: 1), c-myc (SEQ ID NO: 2) and V5 (SEQ ID NO: 3) are directly linked.

89. The library of embodiment 87, wherein the 6× histidine (SEQ ID NO: 1), c-myc (SEQ ID NO: 2) and V5 (SEQ ID NO: 3) are indirectly linked through a spacer.

90. The library of embodiment 89, wherein the spacer is 3 to 7 amino acids in length.

91. The library of embodiment 90, wherein the spacer is GM or KAA.

92. The library of embodiment 88, wherein the triple tag sequence is represented by HHHHHHEQKLISEEDLGKPIPNPLLGLDST (SEQ ID NO: 4).

93. The library of embodiment 89, wherein the triple tag sequence is represented by HHHHHHGAAEQKLISEED-LKAAGKPIPNPLLGLDST (SEQ ID NO: 5).

94. A plurality of polynucleotides encoding a Fab library, the library comprising a plurality of vectors wherein each vector of the plurality of vectors comprises:
a polynucleotide comprising sequences encoding an antibody heavy chain variable region, an antibody heavy chain constant region, a light chain variable region and a light chain constant region, and wherein the polynucleotide further comprises a sequence encoding a triple tag sequence comprising 6× histidine (SEQ ID NO: 1), c-myc (SEQ ID NO: 2) and V5 (SEQ ID NO: 3).

95. A plurality of polynucleotides encoding a single chain antibody library, the library comprising a plurality of vectors wherein each vector of the plurality of vectors comprises:
a polynucleotide comprising sequences encoding an antibody heavy chain variable region, and a light chain variable region, and wherein the polynucleotide further comprises a sequence encoding a triple tag sequence comprising 6× histidine (SEQ ID NO: 1), c-myc (SEQ ID NO: 2) and V5 (SEQ ID NO: 3).

96. The library of embodiments 94-95, wherein the 6× histidine (SEQ ID NO: 1), c-myc (SEQ ID NO: 2) and V5 (SEQ ID NO: 3) are directly linked.

97. The library of embodiments 94-95, wherein the 6× histidine (SEQ ID NO: 1), c-myc (SEQ ID NO: 2) and V5 (SEQ ID NO: 3) are indirectly linked through a spacer.

98. The library of embodiment 97, wherein the spacer is 3 to 7 amino acids in length.

99. The library of embodiment 98, wherein the spacer is GM or KAA.

100. The library of embodiment 96, wherein the triple tag sequence is represented by HHHHHHEQKLISEEDLGK-PIPNPLLGLDST (SEQ ID NO: 4).

101. The library of embodiment 97, wherein the triple tag sequence is represented by HHHHHHGAAEQKLISEED-LKAAGKPIPNPLLGLDST (SEQ ID NO: 5).

102. A method for screening a library of bacteriophage according to embodiment 75 comprising a plurality of proteins of interest linked to a triple tag sequence comprising 6× histidine (SEQ ID NO: 1), c-myc (SEQ ID NO: 2) and V5 (SEQ ID NO: 3), said method comprising:
(a) contacting a sample of the library with a first binding molecule specific for a 6× histidine, a c-myc tag, or a V5 tag;
(b) capturing the proteins of interest linked to the triple tag sequence with the binding molecule specific for the 6× histidine tag, c-myc tag, or V5 tag;
(c) contacting the bound protein of interest with a second binding molecule specific for 6× histidine tag, c-myc tag, or V5 tag; and
(d) detecting the protein of interest with a binding molecule specific for 6× histidine tag, c-myc tag, or V5 tag,
wherein the specificity of the first binding molecule is different than the specificity of the second binding molecule.

103. The method of embodiment 102, wherein a binding molecule specific for V5 is used in step (a) and a binding molecule specific for 6× histidine is used in step (c).

104. The method of embodiment 102, wherein a binding molecule specific for 6× histidine is used in step (a) and a binding molecule specific for V5 histidine is used in step (c).

105. A method for screening a library of bacteriophage according to embodiment 75 comprising a plurality of proteins of interest linked to a triple tag sequence comprising 6× histidine (SEQ ID NO: 1), c-myc (SEQ ID NO: 2) and V5 (SEQ ID NO: 3), said method comprising:
(a) contacting a sample of the library with a first binding molecule specific for a 6× histidine, a c-myc tag, or a V5 tag;
(b) detecting the proteins of interest linked to the triple tag sequence with the binding molecule specific for the 6× histidine tag, c-myc tag, or V5 tag;
(c) contacting the bound protein of interest with a second binding molecule specific for 6× histidine tag, c-myc tag, or V5 tag; and
(d) detecting the protein of interest with a binding molecule specific for 6× histidine tag, c-myc tag, or V5 tag,
wherein the specificity of the first binding molecule is different than the specificity of the second binding molecule.

106. The method of embodiment 105, wherein a binding molecule specific for V5 is used in step (a) and a binding molecule specific for 6× histidine is used in step (c).

107. The method of embodiment 105, wherein a binding molecule specific for 6× histidine is used in step (a) and a binding molecule specific for V5 histidine is used in step (c).

While the present disclosure has been described and illustrated herein by references to various specific materials, procedures and examples, it is understood that the disclosure is not restricted to the particular combinations of materials and procedures selected for that purpose. Numerous variations of such details can be implied as will be appreciated by those skilled in the art. It is intended that the specification and examples be considered as exemplary, only, with the true scope and spirit of the disclosure being indicated by the following claims. All references, patents, and patent applications referred to in this application are herein incorporated by reference in their entirety.

The invention claimed is:

1. A method of screening a phagemid library of proteins of interest, wherein the library comprises a plurality of vectors which each comprise a polynucleotide coding for a protein of interest linked to a polynucleotide coding for a triple tag sequence, wherein the triple tag sequence comprises 6X histidine (SEQ ID NO: 1), c-myc (SEQ ID NO: 2) and V5 (SEQ ID NO: 3), said method comprising:

(a.) expressing a plurality of proteins of interest linked to the triple tag sequence from the plurality of vectors;

(b.) screening the proteins of interest linked to the triple tag sequence for binding to a binding partner of the protein of interest; and (c.) recovering the proteins of interest linked to the triple tag sequence that are bound in step (b.) by capture with an antibody specific for V5, c-myc or 6X histidine, wherein the triple tag sequence is HHHHHHGAAEQKLISEEDLKAAGKPIPNPLLGLDST (SEQ ID NO: 5), and wherein the protein of interest is a single chain antibody.

* * * * *